(12) United States Patent
Shea et al.

(10) Patent No.: US 11,458,107 B2
(45) Date of Patent: Oct. 4, 2022

(54) ABIOTIC ANTI-VEGF NANOPARTICLE

(71) Applicants: THE REGENTS OF THE UNIVERSITY OF CALIFORNIA, Oakland, CA (US); Yoshiko Miura, Fukuoka (JP); Yu Hoshino, Fukuoka (JP); Yuri Nishimura, Fukuoka (JP); Naoto Oku, Shizuoka (JP)

(72) Inventors: Kenneth J. Shea, Irvine, CA (US); Hiroyuki Koide, Shizuoka (JP); Yoshiko Miura, Fukuoka (JP); Yu Hoshino, Fukuoka (JP); Yuri Nishimura, Fukuoka (JP); Naoto Oku, Shizuoka (JP)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/327,898

(22) PCT Filed: Aug. 25, 2017

(86) PCT No.: PCT/US2017/048528
§ 371 (c)(1),
(2) Date: Feb. 25, 2019

(87) PCT Pub. No.: WO2018/039509
PCT Pub. Date: Mar. 1, 2018

(65) Prior Publication Data
US 2019/0216744 A1  Jul. 18, 2019

Related U.S. Application Data

(60) Provisional application No. 62/379,584, filed on Aug. 25, 2016.

(51) Int. Cl.
*A61K 9/51*  (2006.01)
*A61K 31/795*  (2006.01)
(Continued)

(52) U.S. Cl.
CPC .......... *A61K 9/5146* (2013.01); *A61K 9/0019* (2013.01); *A61K 31/704* (2013.01);
(Continued)

(58) Field of Classification Search
CPC .. A61K 9/5146; A61K 31/785; A61K 31/704; A61K 31/795; A61K 9/0019; A61P 35/00
See application file for complete search history.

(56) References Cited

U.S. PATENT DOCUMENTS

2008/0269105 A1* 10/2008 Taft ...................... A61K 9/0024
514/1.1

FOREIGN PATENT DOCUMENTS

CN    105817268 A  *  8/2016
JP    2012250168 A  *  12/2012

* cited by examiner

*Primary Examiner* — Jianfeng Song
(74) *Attorney, Agent, or Firm* — Riverside Law LLP

(57) ABSTRACT

The present invention relates generally to compositions and methods comprising abiotic, synthetic polymers with affinity and specificity to proteins. The synthetic polymers are an improvement over biological agents by providing a simpler, less expensive, and customizable platform for binding to proteins. In one embodiment, the compositions and methods relate to synthetic polymers with affinity and specificity to vascular endothelial growth factor (VEGF). In one embodiment, the compositions are useful for treating diseases and disorders related to the overexpression of VEGF. In one embodiment, the compositions are useful for treating cancer. In one embodiment, the compositions are useful for detecting VEGF levels from biological samples. In one embodiment, the compositions are useful for detecting overexpres- (Continued)

sion of VEGF from biological samples. In one embodiment, the compositions are used to diagnose cancer.

8 Claims, 18 Drawing Sheets

(51) Int. Cl.
*A61P 35/00* (2006.01)
*A61K 31/785* (2006.01)
*A61K 31/704* (2006.01)
*A61K 9/00* (2006.01)

(52) U.S. Cl.
CPC .......... *A61K 31/785* (2013.01); *A61K 31/795* (2013.01); *A61P 35/00* (2018.01)

2A

| | NIPAm | AS | TBAm | Bis | Size (nm) | PDI | ζ-potential (mV) |
|---|---|---|---|---|---|---|---|
| NP1 | 58 | 0 | 40 | 2 | 79.9 | 0.014 | N.D. |
| NP2 | 56.3 | 1.7 | 40 | 2 | 62.7 | 0.120 | -32.5 |
| NP3 | 53 | 5 | 40 | 2 | 52.7 | 0.313 | -32.2 |
| NP4 | 48 | 10 | 40 | 2 | 62.5 | 0.351 | -36.4 |

2B

| | NIPAm | 3S-GlcNAc | TBAm | Bis | Size (nm) | PDI | ζ-potential (mV) |
|---|---|---|---|---|---|---|---|
| NP5 | 56.3 | 1.7 | 40 | 2 | 86.7 | 0.053 | -30.7 |
| NP6 | 53 | 5 | 40 | 2 | 81.2 | 0.045 | -33.8 |

2C

| | NIPAm | 4S-GlcNAc | TBAm | Bis | Size (nm) | PDI | ζ-potential (mV) |
|---|---|---|---|---|---|---|---|
| NP7 | 56.3 | 1.7 | 40 | 2 | 52.0 | 0.070 | -41.0 |
| NP8 | 53 | 5 | 40 | 2 | 55.0 | 0.145 | -42.0 |

2D

| | NIPAm | 6S-GlcNAc | TBAm | Bis | Size (nm) | PDI | ζ-potential (mV) |
|---|---|---|---|---|---|---|---|
| NP9 | 56.3 | 1.7 | 40 | 2 | 57.1 | 0.066 | -40.4 |
| NP10 | 53 | 5 | 40 | 2 | 34.1 | 0.198 | -34.3 |

2E

| | NIPAm | 3,4,6S-GlcNAc | TBAm | Bis | Size (nm) | PDI | ζ-potential (mV) |
|---|---|---|---|---|---|---|---|
| NP11 | 56.3 | 1.7 | 40 | 2 | 85.9 | 0.017 | -38.1 |
| NP12 | 53 | 5 | 40 | 2 | 87.7 | 0.026 | -31.1 |
| NP13 | 48 | 10 | 40 | 2 | 74.8 | 0.044 | -29.7 |

ABIOTIC ANTI-VEGF NANOPARTICLE

CROSS-REFERENCE TO RELATED APPLICATIONS

This application is the U.S. national phase application filed under 35 U.S.C. § 371 claiming benefit to International Patent Application No. PCT/US17/48528 filed Aug. 25, 2017, which is entitled to priority under 35 U.S.C. § 119(e) to U.S. Provisional Patent Application No. 62/379,584 filed Aug. 25, 2016, the contents of which are each incorporated by reference herein in their entirety.

STATEMENT REGARDING FEDERALLY SPONSORED RESEARCH OR DEVELOPMENT

This invention was made with government support under grant number DMR-1308363 awarded by the National Science Foundation. The government has certain rights in the invention.

BACKGROUND OF THE INVENTION

Protein affinity reagents are widely used in basic research, industrial processes and clinical applications for isolation of individual proteins, for analytical or diagnostic purposes, and for their effect on biological systems by modulating the function of the target protein for mechanistic research or for therapeutic intervention. Antibodies or their fragments are the most common protein affinity reagents (Hardiman, G., P Natl Acad Sci USA (2012) 109:18245-18246). In addition, there are now a number of new technologies that are being developed to generate affinity reagents including antibody-like molecules that utilize novel protein scaffolds (Dubel, S. et al., Trends Biotechnol (2010) 28:333-339), oligomers (e.g., RNA and DNA aptamers) (Lollo, B. et al., Proteomics (2014), 14:638-644), native or synthesized amino acid polypeptides (Cobaugh, C. W. et al., J Mol Biol (2008) 378:622-633), and various hybrids of these forms (Marx, V., Nat Methods (2013) 10:829-833). Despite the variety of approaches for generating biological affinity reagents, current limitations including time needed for their discovery, development and production, reagent cost, and robustness provide strong motivation to explore non-biological alternatives.

Affinity reagents such as antibodies and related biological macromolecules "recognize" protein surfaces with combinations of 22 proteinogenic amino acids. The affinity is due to the sum total of complementary non-covalent interactions over surfaces that often exceed 1500 Å$^2$ and involve at least 20-30 amino acid contacts from each partner. Unlike well-defined enzyme active sites that can be targeted by small organic molecules (i.e., enzyme inhibitors), protein surfaces are mildly undulating and relatively featureless. An effective non-biological synthetic protein affinity reagent should engage a protein surface with multiple contacts over a substantial surface area, an attribute that challenges discovery of small organic molecular inhibitors of protein-protein complex formation (Arkin, M. R. et al., Nat. Rev. Drug Discov. (2004) 3:301-317).

Synthetic polymers have many features that make them attractive candidates as protein affinity reagents. They can be designed to be large and flexible, properties that allow them to map onto significant portions of a protein surface. In addition, they are relatively simple and inexpensive to produce and can be prepared rapidly on a large scale in the chemistry laboratory. Since their synthesis does not require living organisms, biological contamination is avoided. Organic polymers are robust and can function under a variety of physiological and nonphysiological conditions. A broad range of chemical functionality is available to synthetic polymers permitting opportunities for optimizing affinity. Furthermore the size, physical properties, and biomacromolecule affinity of many polymers can be influenced by external stimuli (temperature, pH, ionic strength) providing an extra dimension of control (Klinger, D. et al., Polymer (2012) 53:5209-5231; Schild, H. G., Progress in Polymer Science (1992) 17:163-249).

However, since synthetic polymers are prepared by a kinetically driven free radical polymerization, the sequence of functional monomers is not controlled. The absence of sequence control may be compensated to some degree by their conformational promiscuity. This would allow optimization of complementary interactions with protein surfaces by an induced fit, a process that finds many analogies in biology (Uversky, V. N. et al., Annu Rev Biophys (2008) 37:215-246; Rogers, J. M. et al., J. Am. Chem. Soc. (2014) 136:5197-5200). Compositional optimization permits "focusing" on a particular biomacromolecule target by adjusting the NPs chemical constituents. A lightly cross-linked network polymer presents 3-dimensional arrays of linear polymer segments that can serve as both continuous and discontinuous recognition elements for binding protein surfaces. Nevertheless, the advantages of synthetic polymers must be tempered by the fact that the polymers are not pure substances; their affinity, for example, is the average of the ensemble of all the polymers in the measurement. In this regard, they may be viewed as primitive polyclonals. Although some success in refining and focusing that distribution has been made (Hoshino, Y. et al., J. Am. Chem. Soc. (2010) 132:13648-13650), challenges remain to demonstrate the ability to produce a polymer NP with affinity to provide a sufficient and consistent level of function.

In recent work, a small but growing body of evidence suggests that synthetic linear polymers (Christman, K. L. et al., J. Am. Chem. Soc. (2008) 130:16585-16591; Oh, Y. I. et al., Angew. Chem. Int. Ed. (2013) 52:11796-11799; Nguyen, T. H. et al. Nat Chem (2013) 5:221-227), dendritic polymers (Dernedde, J. et al. P Natl Acad Sci USA (2010) 107:19679-19684), and polymer nanoparticles (NPs) can be engineered to exhibit strong affinity for a range of target peptides (Hoshino, Y. et al. P Natl Acad Sci USA (2012) 109:33-38; Yoshimatsu, K. et al., Nat protoc (2015) 10:595-604; Koch, S. J. et al., Angew. Chem. Int. Ed. (2006) 45:6352-6355), proteins (Lee, S. H. et al., J. Am. Chem. Soc. (2012) 134:15765-15772; Yoshimatsu, K. et al., Angew. Chem. Int. Ed. (2012) 51:2405-2408), and polysaccharides (Lee, S. H. et al., J. Am. Chem. Soc. (2012) 134:15765-15772). Indeed, polymer nanoparticles have been formulated with nanomolar affinity against target peptides and proteins using only combinations of hydrophobic and charged groups. These interactions mimic those arising from side chains of amino acids. However, nature also uses other functional groups including oligosaccharides, glycosaminoglycans (GAGs), and their post-translationally modified derivatives including phosphorylated and sulfated carbohydrates and proteins to regulate biological function. Incorporation of these functional groups into a synthetic copolymer has the potential to improve affinity and/or broaden target scope. This background provides guidance for the present invention, the rational design of an abiotic protein affinity reagents. It should be noted however, affinity alone may not be sufficient to influence function of a protein associated with maintenance of homeostasis such as a signaling protein, since inhibition of the protein's function requires masking the functional domain. A recent demonstration of this point comes from Maynard et al (Christman, K. L. et al., J. Am. Chem. Soc. (2008) 130:16585-16591; Nguyen, T. H. et al. Nat Chem (2013) 5:221-227). Although a poly(styrene-sulfonate) polymer stabilizes basic fibroblast growth factor (bFGF) by covalent attachment, the polymer did not inhibit the proteins activity (Christman, K. L. et al., J. Am. Chem. Soc. (2008) 130:16585-16591; Nguyen, T. H. et al. Nat Chem (2013) 5:221-227).

Thus there is a need in the art for improved abiotic protein affinity reagents. The present invention satisfies this unmet need.

SUMMARY OF THE INVENTION

The present invention includes an abiotic, synthetic polymer composition, comprising: N-isopropylacrylamide (NIPAm); N-tert-butylacrylamide (TBAm); N,N'-methylenebisacrylamide (Bis); and a sulfated monomer.

In one embodiment, the composition has affinity to vascular endothelial growth factor (VEGF). In one embodiment, the sulfated monomer is a mono-sulfated N-acetylglucosamine (GlcNAc). In one embodiment, the GlcNAc is selected from the group consisting of 3S-GlcNAc, 4S-GlcNAc, and 6S-GlcNAc. In one embodiment, the sulfated monomer is the tri-sulfated N-acetylglucosamine 3,4,6S-GlcNAc. In one embodiment, the composition comprises between 30% and 70% NIPAm. In one embodiment, the composition comprises between 30% and 50%. TBAm. In one embodiment, the composition comprises between 0% and 10% Bis. In one embodiment, the composition comprises between 1% and 20% GlcNAc. In one embodiment, the composition comprises between 1% and 20% 3,4,6S-GlcNAc. In one embodiment, the composition comprises 56.3% NIPAm, 40% TBAm, 2% Bis, and 1.7% 3,4,6S-GlcNAc.

In one embodiment, the composition is a nanoparticle. In one embodiment, the composition further comprises at least one therapeutic agent.

The present invention also includes a method of treating cancer in a subject, comprising administering to a subject a therapeutically effective amount of an abiotic, synthetic polymer composition having affinity to VEGF.

In one embodiment, the composition comprises N-isopropylacrylamide (NIPAm), N-tert-butylacrylamide (TBAm), N,N'-methylenebisacrylamide (Bis), and a sulfated monomer. In one embodiment, the sulfated monomer is a mono-sulfated N-acetylglucosamine (GlcNAc). In one embodiment, the GlcNAc is selected from the group consisting of 3S-GlcNAc, 4S-GlcNAc, and 6S-GlcNAc. In one embodiment, the sulfated monomer is the tri-sulfated N-acetylglucosamine 3,4,6S-GlcNAc. In one embodiment, the composition comprises between 30% and 70% NIPAm. In one embodiment, the composition comprises between 30% and 50%. TBAm. In one embodiment, the composition comprises between 0% and 10% Bis. In one embodiment, the composition comprises between 1% and 20% GlcNAc. In one embodiment, the composition comprises between 1% and 20% 3,4,6S-GlcNAc. In one embodiment, the composition comprises 56.3% NIPAm, 40% TBAm, 2% Bis, and 1.7% 3,4,6S-GlcNAc. In one embodiment, the composition is a nanoparticle. In one embodiment, the composition is administered with a therapeutic agent. In one embodiment, the therapeutic agent is the anti-tumor agent doxorubicin.

The present invention also includes a method of inhibiting angiogenesis in a subject, comprising administering to a subject a therapeutically effective amount of an abiotic, synthetic polymer composition having affinity to VEGF.

In one embodiment, the composition comprises N-isopropylacrylamide (NIPAm), N-tert-butylacrylamide (TBAm), N,N'-methylenebisacrylamide (Bis), and a sulfated monomer. In one embodiment, the sulfated monomer is a mono-sulfated N-acetylglucosamine (GlcNAc). In one embodiment, the GlcNAc is selected from the group consisting of 3S-GlcNAc, 4S-GlcNAc, and 6S-GlcNAc. In one embodiment, the sulfated monomer is the tri-sulfated N-acetylglucosamine 3,4,6S-GlcNAc. In one embodiment, the composition comprises between 30% and 70% NIPAm. In one embodiment, the composition comprises between 30% and 50%. TBAm. In one embodiment, the composition comprises between 0% and 10% Bis. In one embodiment, the composition comprises between 1% and 20% GlcNAc. In one embodiment, the composition comprises between 1% and 20% 3,4,6S-GlcNAc. In one embodiment, the composition comprises 56.3% NIPAm, 40% TBAm, 2% Bis, and 1.7% 3,4,6S-GlcNAc. In one embodiment, the composition is a nanoparticle. In one embodiment, the method is capable of treating cancer. In one embodiment, the composition is administered with a therapeutic agent. In one embodiment, the therapeutic agent is the anti-tumor agent doxorubicin.

The present invention also includes a method of detecting cancer in a subject, comprising the steps of: acquiring a biological sample from the subject; and quantifying the amount of VEGF present in the biological sample using an abiotic, synthetic polymer composition having affinity to VEGF.

In one embodiment, the composition comprises N-isopropylacrylamide (NIPAm), N-tert-butylacrylamide (TBAm), N,N'-methylenebisacrylamide (Bis), and a sulfated monomer. In one embodiment, the biological sample is a fluid sample.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

(FIG. 1C) TEM image of NP11. Bar: 1 μm. (FIG. 1D) High magnification TEM image of NP11. Bar: 100 nm.

FIG. 2A through FIG. 2E is a table depicting monomer composition, size, zeta-potential, and yield of the NPs. The monomer structures can be found in FIG. 1A and FIG. 1B. (FIG. 2A) AS, (FIG. 2B) 3S-GlcNAc, (FIG. 2C) 4S-GlcNAc, (FIG. 2D) 6S-GlcNAc and (FIG. 2E) 3,4,6S-GlcNAc. N.D.; Not determined.

FIG. 3A depicts 3,4,6S-GlcNAc; FIG. 3B depicts 3S-GlcNAc; FIG. 3C depicts 4S-GlcNAc; FIG. 3D depicts 6S-GlcNAc). Incorporation percentage was calculated by 1HNMR.

NP interaction. The surface of the QCM was functionalized with $VEGF_{165}$ and solutions of NPs were added to the QCM cells. (FIG. 4A) $VEGF_{165}$ affinity of NP1-NP4. (FIG. 4B) $VEGF_{165}$ affinity of NP5, NP7 and NP9. (FIG. 4C) $VEGF_{165}$ affinity of NP6, NP8 and NP10. (FIG. 4D) $VEGF_{165}$ affinity of NP1, NP11, NP12 and NP13.

(FIG. 5A) Affinity of BSA to NP1, NP11-NP13. The surface of the QCM was functionalized with BSA and solutions of NPs were added to the QCM cells. NP1 (Purple); NP11 (Red); NP12 (Blue); NP13 (Green). (FIG. 5B) Affinity of $VEGF_{165}$ to NP2. The surface of the QCM was functionalized with $VEGF_{165}$ and solutions of NP11 or PBS was added to the QCM cells. After washing with PBS, $VEGF_{165}$ was added into NP11 immobilized QCM cell to demonstrate binding affinity of $VEGF_{165}$ to NP11. NP11 (Red); PBS (Black).

(FIG. 8A) Inhibition of $VEGF_{165}$-dependent VEGFR-2 phosphorylation by NP11. (FIG. 8B) Inhibition of $VEGF_{165}$-dependent cell growth by NP1, NP11-NP13. Significant differences: $*p<0.05$ and $***p<0.001$ vs. 0 µg/mL. (FIG. 8C) Factor Xa (FXa) binding study to AT III. After incubation of AT III with several concentration of NP11, UFH or LMWH (Dalteparin), FXa was added. Then, the remaining FXa was measured. (FIG. 8D) Inhibition of $VEGF_{165}$-dependent cell growth heparin (UFH or LMWH (dalteparin)) Significant differences: $*p<0.05$ and $***p<0.001$ vs. 0 µg/mL.

(FIG. 12A) Inhibition of $VEGF_{165}$-dependent cell motility by NP1, NP11-NP13. Bar: 30 µm. (FIG. 12B) Inhibition of $VEGF_{165}$-dependen capillary tube formation in the presence of NP1, NP11-NP13. Bar: 30 µm. (FIG. 12C) Inhibition of in vivo angiogenesis in Matrigel plugs implanted in mice. Plugs were removed from mice and photographed after 10 days. (FIG. 12D) Hemoglobin (Hb) content within Matrigel plugs was quantified and depicted as the percent of Hb. Significant differences: $***p<0.001$ vs. Control (+)

(FIG. 15A) Heparin and $VEGF_{165}$ interaction. (FIG. 15B) $VEGF_{165}$ interaction with NPs that lack TBAm, a hydrophobic monomer (NP15). (FIG. 15C) $VEGF_{165}$ interaction with NPs containing TBAm and 5% Monosulfated GlcNAc monomer (NP10). (FIG. 15D) $VEGF_{165}$ interaction with NPs containing TBAm and 1.7% 3,4,6 tri-sulfated monomer containing (NP11).

(FIG. 16A) Biodistribution of 14C labeled NP11 in tumor-bearing mice at 30 min or 1 hour after the intravenous injection of NP11. (FIG. 16B) Biodistribution of 14C labeled NP11 in normal mice at 2 or 4 weeks after the intravenous injection of NP11. (FIG. 16C through FIG. 16E) Therapeutic effect of NP11 using tumor-bearing mice. (FIG. 16C) The mice were intravenously injected with PBS or NP11 (5, 10, 20 or 40 mg/kg) at 5, 7, 9, and 11 days after tumor implantation. Significant difference: $*p<0.05$; Control vs 10 or 20 mg/kg, $p<0.01$; Control vs 40 mg/kg. (FIG. 16D, FIG. 16E) The mice were intravenously injected with NP11 (20 or 40 mg/kg,) at day 5, 7, 9 and 11 days, and doxorubicin ((FIG. 16D) 2.5 or (FIG. 16E) 5 mg/kg) at day 6, 8, 10 and 12 days after the tumor inoculation. Black arrows show NPs injection day. Red arrows show Dox injection day. Significant differences: $*p<0.01$; vs PBS, # $p<0.05$; vs Dox and ## $p<0.01$; vs Dox. (FIG. 16F) Blood perfusion efficiency. Lectin perfusion and CD31 staining of Colon tumor sections. Green color indicates CD31 positive cells, red color indicates lectin positive cells and yellow color indicates double-stained vessel area. White bar shows 50 µm. (FIG. 16G) Dox concentration in tumor after the final Dox injection. Significant difference: $*p<0.05$; Dox alone vs NP11 and Dox.

DETAILED DESCRIPTION

Figures 1A, 1B, 1C, 1D:
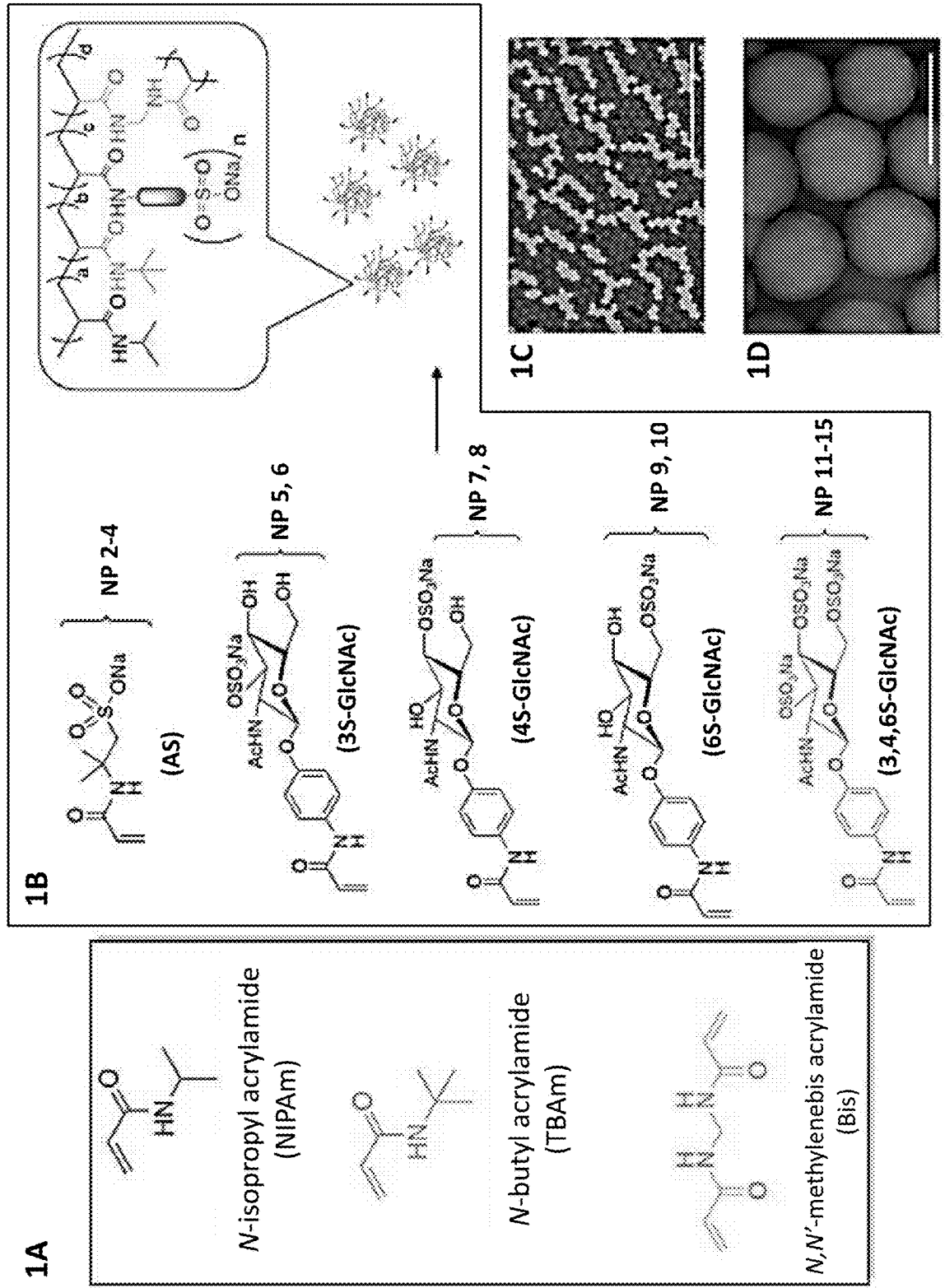
FIG. 1A through FIG. 1D depict the functional (FIG. 1A) and sulfonate and sulfated (FIG. 1B) monomers used for nanoparticle synthesis and a schematic showing the general synthesis of polymer nanoparticles (NP) and their chemical composition. Nanoparticle numbering is correlated with the functional anionic monomer used.
Figure 3A:
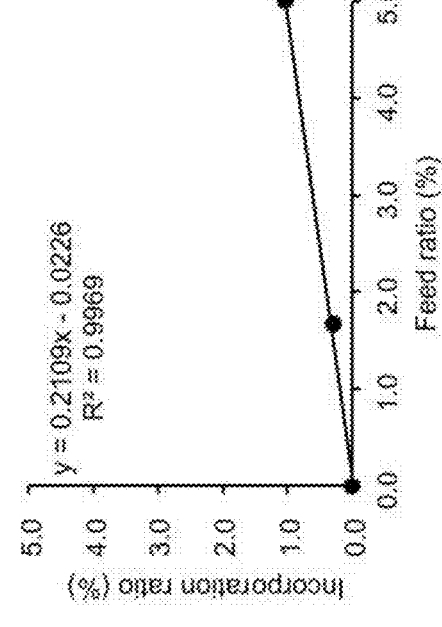
FIG. 3A through FIG. 3D are a series of graphs depicting the relationship between feed and incorporate percentage of sulfonate monomer in NPs.
Figure 3B:
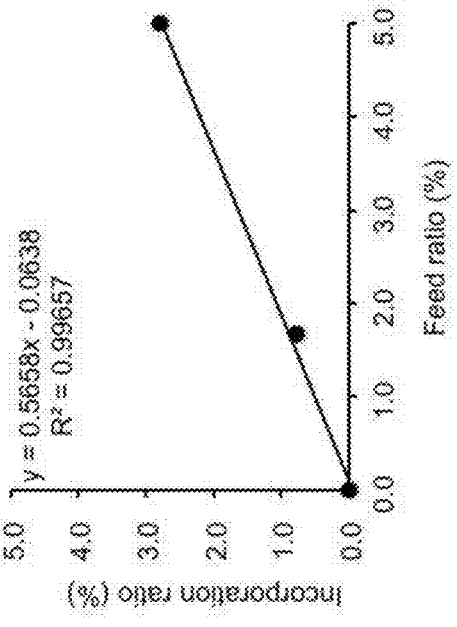
Figure 3C:
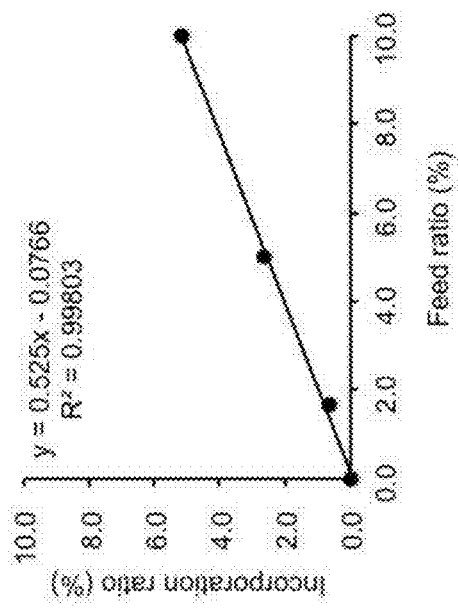
Figure 3D:
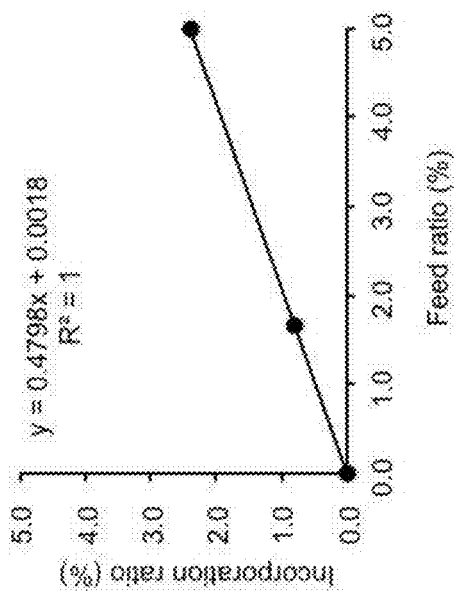

The present invention relates to compositions and methods comprising abiotic, synthetic polymers with affinity and specificity to proteins. The synthetic polymers are an improvement over biological agents by providing a simpler, less expensive, and customizable platform for binding to proteins. In one embodiment, the compositions and methods relate to synthetic polymers with affinity and specificity to vascular endothelial growth factor (VEGF).

In one embodiment, the compositions are useful for treating diseases and disorders related to the overexpression of VEGF. In one embodiment, the compositions are useful for treating cancer. In one embodiment, the compositions are useful for detecting VEGF levels from biological samples. In one embodiment, the compositions are useful for detecting overexpression of VEGF from biological samples. In one embodiment, the compositions are used to diagnose cancer.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells, or components thereof refers to those organisms, tissues, cells, or components thereof that differ in at least one observable or detectable characteristic (e.g., age, treatment, time of day, etc.) from those organisms, tissues, cells, or components thereof that display the "normal" (expected/homeostatic) respective characteristic. Characteristics which are normal or expected for one cell, tissue type, or subject might be abnormal for a different cell or tissue type.

As used herein, a "disease" is a state of health of an individual wherein the individual cannot maintain homeostasis, and wherein if the disease is not ameliorated then the individual's health continues to deteriorate.

As used herein, a "disorder" in an individual is a state of health in which the individual is able to maintain homeostasis, but in which the individual's state of health is less favorable than it would be in the absence of the disorder. Left untreated, a disorder does not necessarily cause a further decrease in the individual's state of health.

As used herein, the term "treating" means ameliorating the effects of, or reducing, delaying, halting, reversing, diminishing, or eliminating the frequency or the occurrence or the severity of at least one sign or symptom of a disease or disorder.

As used herein, the terms "effective amount" or "therapeutically effective amount" or "pharmaceutically effective amount" of a composition are used interchangeably to refer to the amount of the composition that is sufficient to provide a beneficial effect to the subject to which the composition is administered. An appropriate therapeutic amount in any individual case may be determined by one of ordinary skill in the art using routine experimentation.

As used herein, a "therapeutic" treatment is a treatment administered to an individual who exhibits signs or symptoms of a disease or disorder for the purpose of ameliorating the effects of, or reducing, delaying, halting, reversing, diminishing, or eliminating the frequency or occurrence or the severity of at least one of those signs or symptoms.

As used herein, the term "pharmaceutically acceptable" refers to a material, such as a carrier or diluent, that does not abrogate the biological activity or properties of a compound and is relatively non-toxic; i.e., the material may be administered to an individual without causing undesirable biological effects or interacting in a deleterious manner with any of the components of a composition in which it is contained.

As used herein, a "pharmaceutically acceptable carrier" means a pharmaceutically acceptable material, composition, or carrier, such as a liquid or solid filler, diluent, excipient, solvent, or encapsulating material, involved in carrying or transporting at least one compound of the present invention within or to the subject such that it can perform its intended function. Each carrier must be "acceptable" in the sense of being compatible with the other ingredients of the formulation, and not be injurious to the patient. Some examples of materials that can serve as pharmaceutically acceptable carriers include: sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, absorption delaying agents, and the like that are compatible with the activity of a compound and are physiologically acceptable to a subject. Supplementary active compounds can also be incorporated into the compositions.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the terms "subject" or "individual" or "patient" refers to a human or other mammal (e.g., primate, dog, cat, goat, horse, pig, mouse, rat, rabbit, and the like) that can have a vascular endothelial growth factor (VEGF) overexpression-related condition or be at risk for developing a VEGF overexpression-related condition, but may or may not have a VEGF overexpression-related condition or be at risk for developing a VEGF overexpression-related condition.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

The present invention provides compositions comprising abiotic, synthetic polymers with affinity and specificity to proteins and methods of use thereof. In certain embodiments, the invention comprises synthetic polymers with affinity and specificity to vascular endothelial growth factor (VEGF). In certain embodiments, the invention is used to detect and/or treat diseases related to VEGF overexpression.

The present invention is partly based upon the discovery that synthetic polymers comprising N-isopropylacrylamide (NIPAm), N-tert-butylacrylamide (TBAm), sulfonated and sulfated monomers, and N, N'-methylenebisacrylamide (Bis) having binding affinity to VEGF. Thus, the synthetic polymers are able to bind to VEGF and inhibit downstream events such as angiogenesis and cancer.

In some embodiments, the sulfonated monomer is 2-acrylamido-2-methylpropane sulfonic acid (AS). In some embodiments, the sulfated monomer is an N-acetylglucosamine (GlcNAc). In various embodiments, the sulfated monomer is an isomer of GlcNAc, including but not limited to 3S-GlcNAc, 4S-GlcNAc, or 6S-GlcNAc. In one embodiment, the sulfated monomer is 3,4,6S-GlcNAc.

In certain embodiments, the synthetic polymer may be described by the ratio of its components. For example, in certain embodiments, the synthetic polymers may comprise between 0 and 10% Bis. In certain embodiments, the synthetic polymers may comprise between 30 and 50% TBAm. In certain embodiments, the synthetic polymers may comprise between 30 and 70% NIPAm. In certain embodiments, the synthetic polymers may comprise between 1 and 20% AS. In certain embodiments, the synthetic polymers may comprise between 1 and 20% 3 S-GlcNAc. In certain embodiments, the synthetic polymers may comprise between 1 and 20% 4S-GlcNAc. In certain embodiments, the synthetic polymers may comprise between 1 and 20% 6S-GlcNAc. In certain embodiments, the synthetic polymers may comprise between 1 and 20% 3,4,6S-GlcNAc. In one embodiment, the synthetic polymers comprise 56.3% NIPAm, 40% TBAm, 2% Bis, and 1.7% 3,4,6S-GlcNAc.

The synthetic polymers described herein may be prepared in any suitable manner. Suitable synthetic methods used to produce the synthetic polymers include, by way of non-limiting example, cationic, anionic, and free radical polymerization. In some instances, when a cationic process is used, the monomer is treated with a catalyst to initiate the polymerization. Optionally, one or more monomers may be used to form a copolymer. In some embodiments, a catalyst is used an initiator, including, e.g., protonic acids (Bronsted acid) or Lewis acids; in the case of using Lewis acids some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In certain embodiments, the synthetic polymers are prepared by free radical polymerization. When a free radical polymerization process is used, the monomer, optionally, the co-monomer, and an optional source of free radicals are provided to trigger the free radical polymerization process. In some embodiments, the source of free radicals are optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture, and reaction time. The polymerization is carried out in any suitable manner, including, e.g., in solution, dispersion, suspension, emulsion, or bulk.

Polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

Particle Size

In certain embodiments, the abiotic, synthetic polymers of the present invention are assembled into nanoparticles (NP). The NP provided herein can have any suitable size. NP sizes may be adjusted to meet specific needs by adjusting the proportion of components contained therein. In specific embodiments, the NP provided herein have an average hydrodynamic diameter of about 10 nm to about 200 nm. In more specific embodiments, the NP provided herein have an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 90 nm, and the like. Particle size can be determined in any suitable manner, including, but not limited to, by gel permeation chromatography (GPC), dynamic light scattering (DLS), electron microscopy techniques (e.g., TEM), and other methods.

Therapeutic Agents

Provided in certain embodiments herein is a NP comprising the abiotic, synthetic polymers of the present invention and at least one therapeutic agent. The NP is capable of binding to VEGF and localizing in regions of increased VEGF expression and accumulation, and is thereby capable of providing sustained drug delivery of the at least one therapeutic agent. Thus, the NP can provide targeted drug delivery to regions of increased VEGF expression and accumulation. In one embodiment, the at least one therapeutic agent comprises an anti-tumor agent. The therapeutic agent can include any naturally occurring, synthetic, inorganic, organic, peptide, enzyme, nucleic acid small molecule, and the like, which has at least some activity in treating and/or preventing cancer.

Typical anti-tumor agents include, but are not limited to, pyrimidine antimetabolites such as 5-fluorouracil (5FU), tegafur, carmofur, doxifluridine, broxuridine, cytarabine, enocitabine, hydroxypyridine, hydroxycarbamide, methotrexate, fludarabine phosphate and the like; purine antimetabolites such as 6-mercaptopurine, 6-thioguanine, thioinosine, gemcitabine hydrochloride etc., and the like; cisplatin, carboplatin, nedaplatin, oxaliplatin and the like; nitrogen mustard alkylating agents such as nitrogen mustard, nitrogen mustard N-oxide, chlorambucil and the like; ethylenimine derivatives such as carboquone, thiotepa and the like;

sulfonates such as busulfan, improsulfan tosylate and the like; nitrosourea derivatives such as nimustine hydrochloride etc., and the like; mitomycin C, bleomycin, peplomycin, daunorubicin, aclarubicin, doxorubicin, pirarubicin, THP-adriamycin, 4'-epidoxorubicin, epirubicin and the like; chromomycin A3, actinomycin D and the like; *vinca* alkaloids such as vinblastine, vincristine, vindesine and the like; epipodophyllotoxins such as etoposide, teniposide and the like; taxane alkaloids such as paclitaxel, docetaxel etc., and the like; molecule target therapeutic agents including imatinib, gefitinib, erlotinib, vandetanib, sunitinib, sorafenib, rituximab, cetuximab, infliximab, trastuzumab, bevacizumab, and the like, In other embodiments, the present invention is not limited to any particular therapeutic agent, but rather encompasses any suitable therapeutic agent that can be embedded within a NP. Exemplary therapeutic agents include, but are not limited to, anti-viral agents, anti-bacterial agents, chemotherapeutic agents, anti-inflammatory agents, antiseptics, anesthetics, analgesics, pharmaceutical agents, small molecules, peptides, nucleic acids, and the like.

In certain embodiments, the NP described herein comprise at least one antibacterial agent. In one embodiment, the antibacterial agent is a broad-spectrum antibacterial agent. Suitable antibacterial agents include, but are not limited to, chlorhexidine and derivatives thereof, members of the bis-biguanide class of inhibitors, povidone iodine, hydrogen peroxide, doxycycline, minocycline, clindamycin, doxycycline, metronidazole, essential oil extracts (menthol, thymol, eucalyptol, methyl salicylate, metal salts (zinc, copper, stannous ions), phenols (triclosan), all quaternary ammonium compounds (cetylpyridinium chloride), surfactants (sodium lauryl sulphate, delmopinol), all natural molecules (phenols, phenolic acids, quinones, alkaloids, lectins, peptides, polypeptides, indole derivatives, flustramine derivatives, carolacton, halogenated furanones, oroidin analogues, agelasine, ageloxime D).

In various embodiments, the at least one therapeutic agent is attached to the NP in any suitable manner. For example, attachment may be achieved through covalent bonds, non-covalent interactions, static interactions, hydrophobic interactions, or combinations thereof.

In some embodiments, therapeutic agents are selected from, by way of non-limiting example, at least one nucleotide (e.g., a polynucleotide), at least one carbohydrate or at least one amino acid (e.g., a peptide). In specific embodiments, the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In other embodiments, the therapeutic agent is an aiRNA (Asymmetric RNA duplexes mediate RNA interference in mammalian cells. Xiangao Sun, Harry A Rogoff, Chiang J Li Nature Biotechnology 26, 1379-1382 (2008)). In certain embodiments, the therapeutic agent is a protein, peptide, dominant-negative protein, enzyme, antibody, or antibody fragment. In some embodiments, the therapeutic agent is a carbohydrate, or a small molecule. In some embodiments, the therapeutic agent is an abiotic, synthetic polymer.

In some embodiments, a therapeutic agent is chemically conjugated to the NP and/or to one or more polymer of the NP by any suitable chemical conjugation technique. Therapeutic agents are optionally conjugated to an end of the polymer, or to a pendant side chain of the polymer. In some embodiments, NP containing a therapeutic agent are formed by conjugation of the agent with a polymer and subsequently forming the NP in any suitable manner, e.g., by self-assembly of the resulting conjugates into a NP comprising the agent. The covalent bond between a polymer and a therapeutic agent of a NP described herein is, optionally, non-cleavable, or cleavable. In some embodiments, conjugation is also performed with pH-sensitive bonds and linkers, including, but not limited to, hydrazone and acetal linkages.

In certain embodiments, the NP of the invention comprise a therapeutically effective amount of at least one therapeutic agent. For example, in one embodiment, the core of the NP is loaded with a therapeutically effective amount of at least one therapeutic agent. The relative amount or concentration of the therapeutic agent may be dependent upon the size of the NP, type of therapeutic agent, condition to be treated or prevented, and the like. In one embodiment, the therapeutic agent is present at greater than about 0 wt %, or greater than about 5 wt %, or greater than about 10 wt %, or greater than about 15 wt %, or greater than about 20 wt %, or greater than about 30 wt %, or greater than about 50 wt %, or greater than about 75 wt %. For example, it is demonstrated herein that the NP of the invention may loaded with an amount or concentration of a therapeutic agent that is much greater than its minimum effective concentration. Thus, the composition of the invention is able to retain therapeutically effective amounts of a therapeutic agent within the NP.

In certain embodiments, the composition comprises a plurality of different NPs, each carrying a different therapeutic agent, thereby providing combination therapy. For example, in one embodiment, the composition comprises a first NP, comprising an anti-tumor agent, and a second NP, comprising a chemotherapeutic agent. In another embodiment, the composition comprises a first NP, comprising an anti-tumor agent, a second NP, comprising a chemotherapeutic agent, and a third NP, comprising an anti-inflammatory agent. Each therapeutic agent has different yet complementary mechanisms of action, all aimed at treating the pathology. In one embodiment, the different NPs are mixed in different proportions to achieve maximum therapeutic effect. In one embodiment, each of the different NPs can be configured for different drug delivery characteristics, thereby allowing different therapeutic agents to be delivered at different times, as necessitated by the particular disorder or treatment.

Pharmaceutical Compositions and Formulations

The invention also encompasses the use of pharmaceutical compositions of the invention to practice the methods of the invention. Such a pharmaceutical composition may consist of at least one compound, agent, NP, or NP conjugate of the invention in a form suitable for administration to a subject, or the pharmaceutical composition may comprise at least one compound, agent, NP, or NP conjugate of the invention, and one or more pharmaceutically acceptable carriers, one or more additional ingredients, or some combination of these.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin or any other tissue of a mammal. The route(s) of administration will be readily apparent to the skilled artisan and will depend upon any number of factors including the type and severity of the disease being treated, the type and age of the subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound, agent, NP, or NP conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, the carrier may include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. In one embodiment, the preservative is a combination of about 0.5% to 2.0% benzyl alcohol and 0.05% to 0.5% sorbic acid.

In certain embodiments, the composition includes an anti-oxidant and a chelating agent that inhibits degradation. Antioxidants include BHT, BHA, alpha-tocopherol, and ascorbic acid in the ranges of about 0.01% to 0.3% and BHT in the range of 0.03% to 0.1% of the total weight of the composition. The chelating agent may be present in an amount of from 0.01% to 0.5% of the total weight of the composition. Chelating agents include edetate salts (e.g. disodium edetate) and citric acid in the weight range of about 0.01% to 0.20% and in the range of 0.02% to 0.10% of the total weight of the composition. The chelating agent is useful for chelating metal ions in the composition that may be detrimental to the shelf life of the formulation. Other suitable and equivalent antioxidants and chelating agents may be substituted therefore as would be known to those skilled in the art.

Detection Platforms

The present invention provides platforms for detecting VEGF using synthetic polymers. The synthetic polymers disclosed herein may be used in a manner similar to antibodies for capturing, labeling, detecting, and quantifying VEGF. The detection platforms are therefore useful for diagnosing diseases and conditions related to VEGF expression.

In various embodiments, the synthetic polymers of the present invention may be used in any protein detection platform commonly used in the art. Suitable detection platforms include but are not limited to colorimetric systems, chemiluminescence systems, bioluminescence systems, chemifluorescence systems, autoradiography systems, and immunogold labeling. In any of the suitable detection platforms, the VEGF-specific antibodies may be replaced or supplemented with the synthetic polymers of the present invention for more efficient and cost-effective means of VEGF capturing and/or labeling.

Examples of an assay or methodology where the synthetic polymers of the present invention may be used include, but are not limited to, an immunochromatography assay, an immunodot assay, a Luminex assay, an ELISA assay, an ELISPOT assay, a protein microarray assay, a ligand-receptor binding assay, an immunostaining assay, a Western blot assay, a mass spectrophotometry assay, a radioimmunoassay (MA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzymatic assay, an enzymatic assay employing a detectable molecule, such as a chromophore, fluorophore, or radioactive substrate, a substrate binding assay employing such a substrate, and a protein chip assay.

In certain embodiments, the synthetic polymers of the present invention may be used in a biosensor detection platform. Biosensors typically include a transducer that generates a measurable signal in response to a binding event with a target analyte. The transducers can be any suitable transducer platform, including but not limited to nanosheets, nanoparticles, nanowires, and the like constructed from materials such as graphene, silicon, silver, and the like. By way of non-limiting example, the synthetic polymers of the present invention may be incorporated into the biosensor detection platform by deposition, growth, or grafting onto the transducer platform, or alternatively the transducer platform may be coated with NP comprising the synthetic polymer.

Methods of Use

The present invention provides a method of treating diseases and disorders related to the overexpression of a target molecule. The present invention also provides a method of detecting the level of a target molecule from biological samples and diagnosing diseases and disorders related to the overexpression of a target molecule.

In some embodiments, the target molecule is VEGF. Thus, the present invention provides a method of treating diseases and disorders related to the overexpression of VEGF. The present invention also provides a method of detecting VEGF levels from biological samples and diagnosing diseases and disorders related to the overexpression of VEGF.

As described herein, the synthetic polymers described herein having an affinity and specificity for VEGF, wherein binding of the synthetic polymers to VEGF inhibits downstream events such as angiogenesis. As such, the compositions comprising the synthetic polymers described herein are useful as anti-angiogenesis agents to halt tumor growth. In other embodiments, the affinity of the synthetic polymers to VEGF allows the synthetic polymers to act as a homing composition to provide sustained and localized delivery of therapeutic agents to target sites of VEGF overexpression, such as cancerous tissue.

The method of the invention can be used to treat any type of cancer. Non-limiting examples include B cell lymphoma, T cell lymphoma, myeloma, leukemia, hematopoietic neoplasias, thymoma, lymphoma, sarcoma, lung cancer, non-Hodgkins lymphoma, Hodgkins lymphoma, uterine cancer, adenocarcinoma, breast cancer, pancreatic cancer, lung cancer, renal cancer, bladder cancer, prostate cancer, ovarian cancer, primary or metastatic melanoma, squamous cell carcinoma, basal cell carcimona, hepatocellular carcinoma, brain cancer, angiosarcoma, hemangiosarcoma, head and neck carcinoma, thyroid carcinoma, soft tissue sarcoma, bone sarcoma, testicular cancer, uterine cancer, cervical cancer, gastrointestinal cancer, and the like.

The treatment methods can be in any suitable form, including oral administration, parenteral administration, topical administration, and the like.

Parenteral Administration

As used herein, "parenteral administration" of a composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system.

Methods of Detection

The present invention also relates to a method of detecting a disease or disorder of a subject by assessing the level of VEGF in a biological sample of the subject using the synthetic polymers of the present invention. In another embodiment, the invention is a method of assessing the severity of a disease or disorder of a subject by assessing the level of VEGF in a biological sample of the subject using the synthetic polymers of the present invention. In another embodiment, the invention is a method of monitoring the effect of a treatment of a disease or disorder of a subject by assessing the level of VEGF in a biological sample of the subject using the synthetic polymers of the present invention. In one embodiment, the biological sample of the subject is a cell, tissue, or bodily fluid. Non-limiting examples of bodily fluids in which the level of VEGF can be assessed include, but are not limited to, blood, serum, plasma and urine. In various embodiments, the level of VEGF in the biological sample of the subject is compared with the VEGF level in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of. In various embodiments, the disease or disorder is cancer, inflammation, macular degeneration. In some embodiments, the method of diagnosing includes a further step of treating the patient for the diagnosed disease or disorder.

In various embodiments, the subject is a human subject, and may be of any race, sex and age. Representative subjects include those who are suspected of having experienced a disease or disorder, those who have been diagnosed as having experienced a disease or disorder, those who have been diagnosed as having a disease or disorder, and those who are at risk of developing a disease or disorder.

Information obtained from the methods of the invention described herein can be used alone, or in combination with other information (e.g., disease status, disease history, vital signs, blood chemistry, etc.) from the subject or from the biological sample obtained from the subject.

In other various embodiments of the methods of the invention, the level of VEGF detected by the synthetic polymers of the present invention is determined to be increased when the level of VEGF is increased by at least 10%, by at least 20%, by at least 30%, by at least 40%, by at least 50%, by at least 60%, by at least 70%, by at least 80%, by at least 90%, by at least 100%, by at least 200%, by at least 300%, by at least 400%, by at least 500%, by at least 600%, by at least 700%, by at least 800%, by at least 900%, by at least 1000%, when compared to with a comparator control. In various embodiments, an increased level of VEGF is indicative of a disease or disorder.

In the methods of the invention, a biological sample from a subject is assessed for the level of VEGF using the synthetic polymers of the present invention. The level of VEGF in the biological sample can be determined by assessing the level of binding to the synthetic polymers of the present invention. In some embodiments, the level of VEGF in the biological sample is determined in an assay using the synthetic polymers of the present invention.

In various embodiments, methods of measuring VEGF levels in a biological sample obtained from a patient include, but are not limited to, an immunochromatography assay, an immunodot assay, a Luminex assay, an ELISA assay, an ELISPOT assay, a protein microarray assay, a Western blot assay, a mass spectrophotometry assay, a radioimmunoassay (MA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Synthetic Polymer Protein Affinity Reagents. A Polymer Nanoparticle with Engineered Affinity for a Vascular Endothelial Growth Factor ($VEGF_{165}$)

The following study describes the synthesis of an abiotic hydrogel polymer nanoparticle (NP) that has been engineered with affinity for a key vascular endothelial growth factor ($VEGF_{165}$), a signaling protein that stimulates angiogenesis. $VEGF_{165}$ is a 38 kD protein (pI 7.6) with binding-domains for its receptor (VEGFR-2) and for heparin. Heparin, a polysulfated linear polysaccharide, contains repeating disaccharide units of uronic acid and glucosamine moieties. Candidates with high affinity to $VEGF_{165}$ were identified from a screen of polymer NPs incorporating sulfonic acid, sulfated carbohydrate and hydrophobic functional monomers in a 2% crosslinked NIPAm copolymer (FIG. 1A through FIG. 1D). The process, described in detail below, identified a high affinity functional NIPAm copolymer that both binds to and inhibits the function of $VEGF_{165}$. The results establish a novel path for developing abiotic affinity reagents for functional biomacromolecules.

The materials and methods used in the experiments are now described.

Materials

Mouse VEGF-A165, bovine serum albumin, N-isopropylacrylamide (NIPAm), N,N,N',N'-tetramethylethylenediamine, and sodium dodecyl sulfate (SDS) were purchased from Sigma Aldrich. N,N'-methylenebisacrylamide (BIS) was from Fluka; N-t-butylacrylamide (TBAm) was from ACROS ORGANICS. Anti-VEGF receptor-2 and anti-phospho-VEGF receptor-2 (Tyr 951) rabbit monoclonal antibody (Cell Signaling Technology Inc., Beverly, Mass., USA), anti-β-actin rabbit polyclonal antibody (Sigma-Aldrich), and HRP-conjugated anti-rabbit IgG polyclonal antibody (GE Healthcare Bioscience, Tokyo, Japan) were purchased from the sources indicated. Each antibody was diluted according to the manufacturer's instructions.

Synthesis of GlcNAc Monomers

All aqueous solutions were prepared with ultrapure water (18 M cm$^{-1}$, Millipore System). H$_2$O was MilliQ water in all experiments. The following reagents were used as received: Benzaldehyde dimethyl acetal (PhCH(OMe)$_2$), chloroform-d for NMR, 99.8% atom % D, stabilized with silver foil (CDCl$_3$), deuterium oxide, 99.8% atom % D (D$_2$O), methyl sulfoxide-d$_6$ for NMR (DMSO-d$_6$), with 0.03% TMS, 99.9 atom % D, triethylsilane (Et$_3$SiH) (Acros Organics, Geel, Belgium), benzoyl chloride (BzCl), diethyl ether (Et$_2$O), heparin sodium, methanol (MeOH), potassium carbonate (K$_2$CO$_3$), sodium hydrogen carbonate (NaHCO$_3$), trifluoroacetic acid (TFA) (Kanto Chemical, Tokyo, Japan), 10% palladium(II) carbon (Pd/C) (Kojima Chemicals, Saitama, Japan), sulfur trioxide pyridine complex (SO$_3$—Py), sulfur trioxide trimethylamine complex (SO$_3$—NMe$_3$) (Sigma-Aldrich, Louisiana, Mo., USA), acryloyl chloride, trifluoroacetic anhydride (TFAA) (TCI, Tokyo, Japan), sodium methoxide (NaOMe) (Wako Chemical, Osaka, Japan).

Dowex 50WX8, 50-100 mesh, H form (DOW, Michigan, USA) was converted to Na form with 1N NaOH before use. p-toluenesulfonic acid monohydrate (p-TsOH) (TCI, Tokyo, Japan) was dried in vacuo before use.

p-Nitrophenyl 2-acetamido-2-deoxy-β-D-glucopyranoside (1) and p-(N-acrylamido)phenyl 2-acetamido-2-deoxy-6-sulfo-β-D-glucopyranoside 12 were prepared from 2-acetamido-2-deoxy-β-D-glucopyranose described previously (Chen, H. M. et al., Carbohydr Res (2007) 342:2212-22; Sasaki, K. et al., Bioorg Med Chem Lett (2003) 13:2821-3). p-(N-Acrylamido)phenyl β-D-glucuronide was prepared from p-nitrophenyl 3-D-glucuronide described previously (Miura, Y. et al., Bulletin of the Chemical Society of Japan (2010) 83:1004-1009). The following materials were used as received: glass fiber filter (GF75, ADVANTEC, Ehime, JAPAN)

$^1$H NMR (400 MHz) and $^{13}$C NMR (100 MHz) spectra were recorded in CDCl$_3$, DMSO-d$_6$, D$_2$O at room temperature with a JNM-ECP400 (JEOL, Tokyo, Japan). Mass spectra were obtained in MeOH:H$_2$O=1:1 at room temperature with an ESI-MS LCQ-DECA XP spectrometer (Thermo Scientific, Waltham, Mass., USA).

Syntheses of Sulfated GlcNAc Monomers

Scheme 1. Synthesis of pNP GlcNAc 1$^a$.

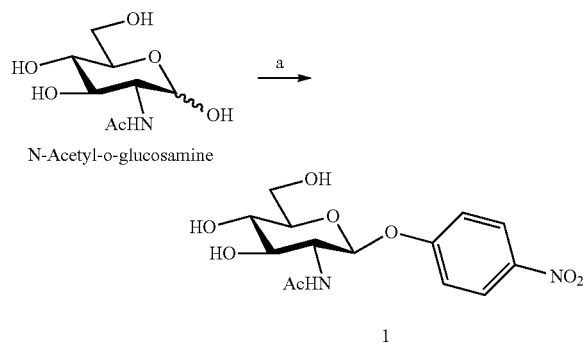

$^a$Reaction conditions: (a) (i) AcCl, 0° C. to room temperature, 24 h, 31%; (ii) p-Nitrophenol, tetra-n-butylammonium bromide, CH$_2$Cl$_2$:1N NaOH = 1:1, room temperature, 4 h, 50%; (iii) NaOMe, MeOH, room temperature, 2 h, >99%.

p-Nitrophenyl 2-acetamido-2-deoxy-β-D-glucopyranoside (1): 1 was prepared from 2-acetamido-2-deoxy-β-D-glucopyranose (GlcNAc) described previously (Chen, H. M. et al., Carbohydr Res (2007) 342:2212-22; Sasaki, K. et al., Bioorg Med Chem Lett (2003) 13:2821-3).

Scheme S2. Synthesis of 3-sulfo GlcNAc monomer 4$^a$.

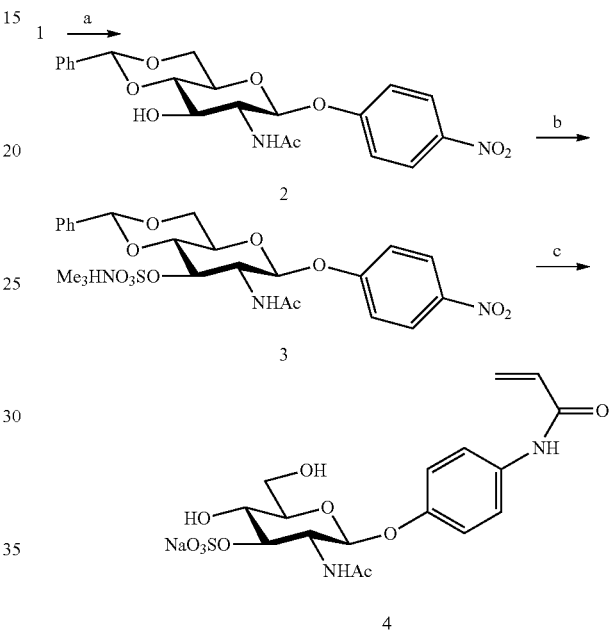

$^a$Reaction conditions: (a) PhCH(OMe)$_2$, p-TsOH, DMF, 40° C., 12 h, 64%; (b) SO$_3$-NMe$_3$, DMF, 40° C., 48 h, 72%; (c) (i) Pd/C, cHCl, H$_2$, MeOH:H$_2$O = 19:1, room temperature, 24 h; (ii) Acryloyl chloride, K$_2$CO$_3$, THF:H$_2$O = 1:2, 0° C. to room temperature, 12 h; (iii) Na form ion exchange resin, H$_2$O, room temperature, 24 h, 25% (in 3 steps).

p-Nitrophenyl 2-acetamido-4,6-O-benzylidene-2-deoxy-β-D-glucopyranoside (2):

Compound 1 (1.00 g, 2.92 mmol) was dissolved in dry DMF (30 mL). PhCH(OMe)$_2$ (530 μL, 3.50 mmol) and p-TsOH (80 mg, 0.438 mmol) were added to the reaction mixture, and the mixture was stirred with a rotary evaporator. The temperature of water bath was defined at 40° C. After 12 h, the termination of the reaction was confirmed by TLC and RP-TLC (CHCl$_3$: MeOH=10:1, H$_2$O:MeOH=2:1, respectively). DMF was removed by evaporation. A saturated aqueous solution of sodium hydrogen carbonate was added to the residue, and the mixture was stirred for 0.5 h at room temperature. The product was filtered off, washed with sufficient amounts of MilliQ water and diethyl ether, and dried in vacuo to afford 2 (801 mg, 64%) as a white solid.

p-Nitrophenyl 2-acetamido-4,6-O-benzylidene-3-sulfo-2-deoxy-β-D-glucopyranoside (3): Compound 2 (940 mg, 2.18 mmol) was dissolved in dry DMF (3 mL). SO$_3$—NMe$_3$ (1.52 g, 10.91 mmol) was added to the solution and the reaction stirred at 40° C. for 72 h. The reaction was quenched by addition of MeOH (20 mL). DMF was removed by evaporation, and purified by flush column chromatography on silica gel with an eluent of (CHCl$_3$:

MeOH=10:1 to 4:1). The eluate was evaporated and the residue was afforded 3 (894 mg, 72%) as a white solid.

p-(N-Acrylamido)phenyl 2-acetamido-2-deoxy-3-sulfo-D-glucopyranoside (4): Compound 3 (894 mg, 1.57 mmol) was dissolved in H$_2$O:MeOH=1:19 (15 mL). Pd/C (90 mg) and concentrated hydrochloric acid (cHCl, 35-37 wt % solution, 681 µL, 7.85 mmol) were then added. The flask was placed in a high pressure vessel which was then pressurized with hydrogen. After 24 h, the termination of the reaction was confirmed by TLC (H$_2$O:MeOH=4:1). Pd/C was removed by filtration with glass fiber filter (GF-75, Advantec, Tokyo, Japan) and the filtrate was evaporated to afford white solid. The residue was dissolved in THF:H$_2$O=1:2 (15 mL), cooled at 0° C., and to the solution were added acryloyl chloride (190 µL, 2.36 mmol) and K$_2$CO$_3$ (651 mg, 4.71 mmol). After stirring 5 minutes, the reaction solution was warmed up to room temperature. The termination of the reaction was confirmed by TLC (H$_2$O:MeOH=4:1). After 12 h, the reaction mixture was neutralized with 1M HCl, evaporated, and purified by reverse-phase chromatography with an eluent of H$_2$O:MeOH=6:1. Eluent fractions were ion-exchanged to Na salt with ion-exchange resin. The solution was freeze dried to afforded 4 (182 mg, 25% in 3 steps) as a white powder.

Scheme S3. Synthesis of 4-sulfo GlcNAc monomer 5$^a$.

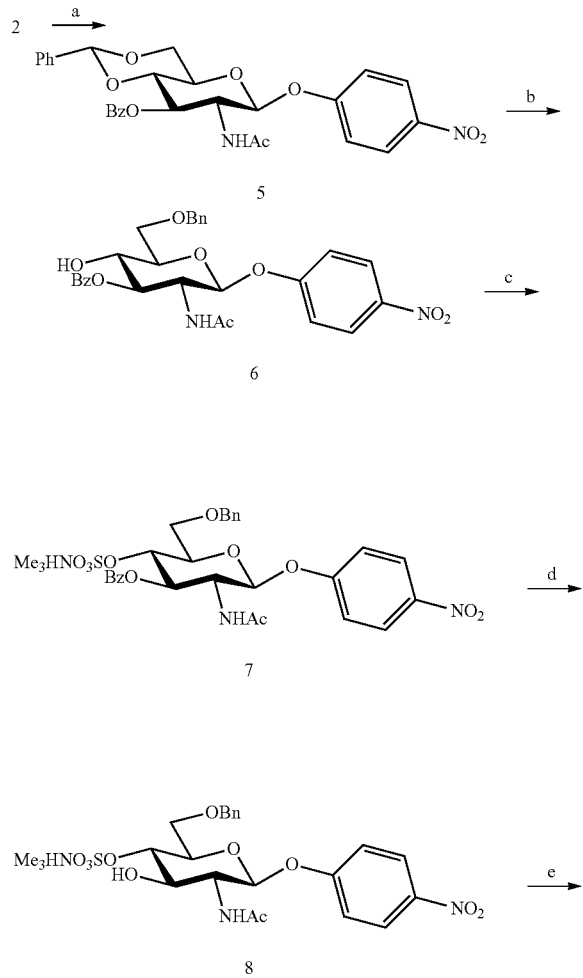

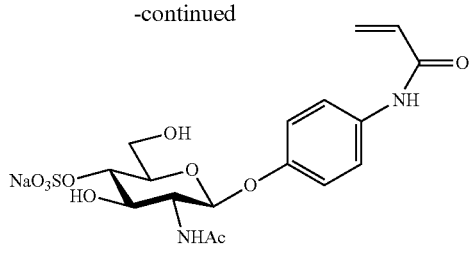

$^a$Reaction conditions: (a) BzCl, pyridine, room temperature, 15 h, >99%; (b) Et$_3$SiH, TFAA, TFA, CH$_2$Cl$_2$, 0° C. to room temperature, 2 h, 87%; (c) Me$_3$NSO$_3$, DMF, 40 to 50° C., 144 h, 92%; (d) NaOMe, MeOH, room temperature, 12 h, 94%; (e) (i) Pd/C, cHCl, H$_2$, MeOH:H$_2$O = 1:1, room temperature, 24 h; (ii) Acryloyl chloride, K$_2$CO$_3$, THF:H$_2$O = 1:2, 0° C. to room temperature, 20 h; (iii) Na form ion exchange resin, H$_2$O, room temperature, 24 h, 42% (in 3 steps).

p-Nitrophenyl 2-acetamido-3-O-benzoyl-4,6-O-benzylidene-2-deoxy-β-D-glucopyranoside (5): Compound 2 (1.06 g, 2.46 mmol) was dissolved in pyridine (15 mL) solution, and BzCl (858 µL, 7.39 mmol) were added to the solution at 0° C. The mixture was stirred at room temperature, and the termination of the reaction was confirmed by TLC (CHCl$_3$:MeOH=10:1). After 15 h, the reaction mixture was quenched by MeOH (10 mL), and the solvent was evaporated. The residue was purified by flush column chromatography on silica gel with an eluent of (CHCl$_3$:MeOH=100:1). The white powder was afforded 5 (1.34 g, >99%).

p-Nitrophenyl 2-acetamido-3-O-benzoyl-6-O-benzyl-2-deoxy-4-hydroxy-β-D-glucopyranoside (6): 5 (297 mg, 0.556 mmol) was suspended in CH$_2$Cl$_2$ (4 mL) added TFAA (232 µL, 1.67 mmol) and Et$_3$SiH (444 µL, 2.78 mmol) at 0° C. After stirring for 15 minutes, TFA (207 µL, 2.78 mmol) was added dropwise and stirred 10 minutes. The reaction mixture was allowed to be warmed up to the ambient temperature. After stirring for overnight, the termination of the reaction was confirmed by TLC (EtOAc:Hexane=1:1). The reaction mixture was diluted by EtOAc and the organic layer was washed NaHCO$_3$, H$_2$O, and brine, respectively. The organic layer was dried on MgSO$_4$, filtrated, and the filtrate was evaporated. The residue was purified by flush column chromatography on silica gel with an eluent of EtOAc:Hexane=1:1 and afforded 6 (260 mg, 87%) as a white solid.

p-Nitrophenyl 2-acetamido-3-O-benzoyl-6-O-benzyl-2-deoxy-4-sulfo-β-D-glucopyranoside (7): The mixture of SO$_3$—NMe$_3$ (1.30 g, 9.32 mmol) in dry DMF (10 mL) was added dropwise to the flask of 6 (50 mg, 0.093 mmol) at 40° C. and the reaction mixture was stirred for 56 h. SO$_3$—NMe$_3$ (777 mg, 5.58 mmol) was added and stirred. After 28 h, reaction temperature was warmed to 50° C. and stirred for 17 h. The reaction was confirmed by TLC (CHCl$_3$:MeOH=3:1), and MeOH (30 mL) was added to the reaction mixture. The mixture was evaporated and the residue was purified by column chromatography on RP-silica gel (Merck, Darmstadt, Germany) with a CHCl$_3$:MeOH=19:1 to 4:1. The white solid was afforded 7 (1.16 g, 92%).

p-(N-Acrylamido)phenyl 2-acetamido-6-O-benzyl-2-deoxy-4-sulfo-β-D-glucopyranoside (8): 7 (923 mg, 1.37 mmol) was dissolved in MeOH (25 mL). NaOMe was added to adjust to pH 10. The termination of the reaction was confirmed with TLC (CHCl$_3$:MeOH=7:3). After 12 h, the reaction was completed and neutralized by Amberlyst (Organo Corporation, Tokyo, Japan). The reaction mixture was filtered, and the filtrate was evaporated. The residue was precipitated with the EtOAc. The white powder was afforded 8 (739 mg, 94%).

p-(N-Acrylamido)phenyl 2-acetamido-2-deoxy-4-sulfo-β-D-glucopyranoside (9): Pd/C (105 mg) and cHCl (0.1 mL) were added to the H$_2$O:MeOH=1:1 (30 mL) solution of 8 (708 mg, 1.24 mmol). The hydrogenation was processed with the autoclave reactor under high hydrogen pressure. After 24 h, the termination of the reaction was confirmed by TLC (CHCl$_3$:MeOH=7:3). Pd/C was removed by filtration with a glass fiber filter and the filtrate was evaporated to afford white solid. The residue was dissolved in THF:H$_2$O=1:2 (12 mL), and cooled at 0° C. To the solution were added acryloyl chloride (150 μL, 1.86 mmol) and K$_2$CO$_3$ (514 mg, 3.72 mmol). After stirring 5 minutes, the reaction mixture was allowed to be warmed up to the ambient temperature. The termination of the reaction was confirmed by TLC (H$_2$O:MeOH=4:1). After 20 h, the reaction mixture was neutralized with 1M HCl, evaporated, and purified by reverse-phase chromatography with a H$_2$O:MeOH=3:1. Eluent fractions were ion-exchanged to Na salt with ion-exchange resin. The solution was freeze dried and purified by reverse-phase chromatography with an eluent of H$_2$O:MeOH=8:1. The solution was freeze dried and afforded 9 (264 mg, 42% in 3 steps) as a white powder.

Preparation of 3,4,6-sulfo GlcNAc monomer 11

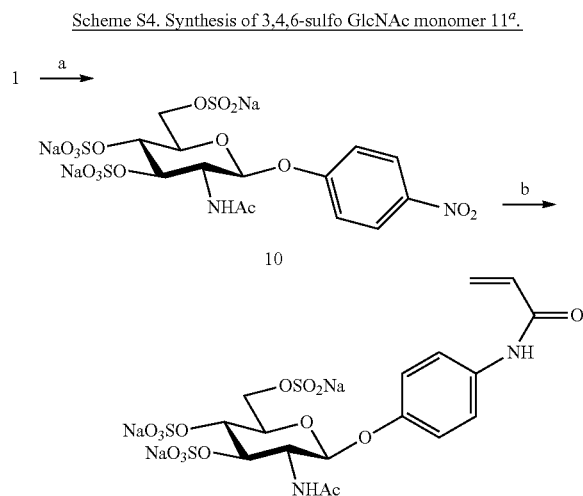

Scheme S4. Synthesis of 3,4,6-sulfo GlcNAc monomer 11$^a$.

$^a$Reaction conditions: (a) (i) SO$_3$-pyridine, pyridine, 40° C., 144 h; (ii) Na form ion exchange resin, H$_2$O, room temperature, 24 h, 99% (in 2 steps); (b) (i) Pd/C, H$_2$, MeOH:H$_2$O = 1:1, room temperature, 25 h; (ii) Acryloyl chloride, K$_2$CO$_3$, THF:H$_2$O = 1:2, 0° C. to room temperature, 12 h >99% (in 2 steps).

p-Nitrophenyl 2-acetamido-2-deoxy-3,4,6-sulfo-β-D-glucopyranoside (10): 1 (500 mg, 1.46 mmol) was dissolved in pyridine, and to the solution was added SO$_3$-Py (2.32 g, 14.6 mmol). The termination of the reaction was confirmed by TLC (CHCl$_3$:MeOH=1:1). After 144 h, MeOH (30 mL) was added. The reaction mixture was passed through an ion-exchange column. The eluent fractions were evaporated, and the residue purified column chromatography on RP-silica gel (H$_2$O:MeOH=9:1). After evaporation of eluent fractions the residue was ion-exchanged to Na salt. The solution was evaporated and freeze dried to afford 10 (938 mg, 99%) as a white powder.

p-(N-Acrylamido)phenyl 2-acetamido-2-deoxy-3,4,6-sulfo-β-D-glucopyranoside (11): 10 (860 mg, 1.33 mmol) was dissolved in a mixture of H$_2$O:MeOH=1:1 (50 mL). To the solution were added Pd/C (90 mg) and CHCl (0.1 mL). The hydrogenation was performed with an autoclave under high hydrogen pressure. After 25 h, the termination of the reaction was confirmed by RP-TLC (H$_2$O:CH$_3$COOH=95:5). Pd/C was removed by filtration with a glass fiber filter, and the filtrate was evaporated to afford a white solid. The residue was dissolved in a mixture of THF:H$_2$O=1:2 (10 mL), cooled at 0° C., and to the solution was added acryloyl chloride (176 μL, 2.18 mmol) and K$_2$CO$_3$ (601 mg, 4.35 mmol). After stirring 5 minutes, the reaction mixture was allowed to be warmed up to the ambient temperature. After 12 h, the termination of the reaction was confirmed by RP-TLC (H$_2$O:CH$_3$COOH=95:5). The reaction solution was neutralized with 1M HCl, evaporated. The residue was purified by column chromatography on RP-silica gel with an eluent of H$_2$O:MeOH=9:1. The residue was dissolved in H$_2$O and freeze dried and afforded 11 (1.07 g, >99% in 2 steps) as a white powder.

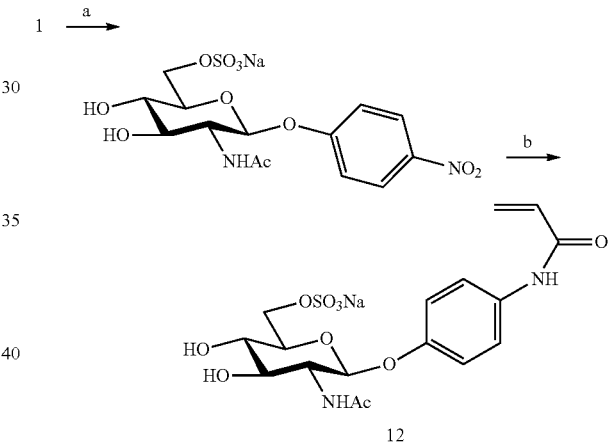

Scheme S5 Syntehsis of 6-sulfo GlcNAc monomer 12$^a$.

$^a$Reaction conditions: (a) (i) Me$_3$NSO$_3$, DMF, 40° C., 0.5 h; (ii) Na form exchange resin, H$_2$O, room temperature, 24 h, 67% (in 2 steps); (b) (i) Pd/C, H$_2$, MeOH:H$_2$O = 1:1, room temperature, 2 h; (ii) Acryloyl chloride, K$_2$CO$_3$, THF:H$_2$O = 1:2, 0° C. to room temperature, 6 h, 68% (in 2 steps).

p-(N-Acrylamido)phenyl 2-acetamido-2-deoxy-6-sulfo-β-D-glucopyranoside (12): 12 were prepared starting from 2-acetamido-2-deoxy-β-D-glucopyranose was described previously (Chen, H. M. et al., Carbohydr Res (2007) 342:2212-22; Sasaki, K. et al., Bioorg Med Chem Lett (2003) 13:2821-3).

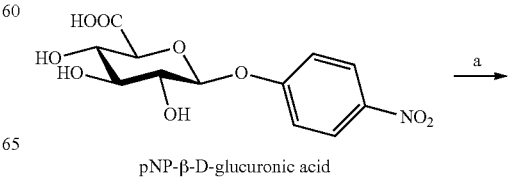

Scheme S6 Synthesis of glucuronic acid monomer 13$^a$.

pNP-β-D-glucuronic acid

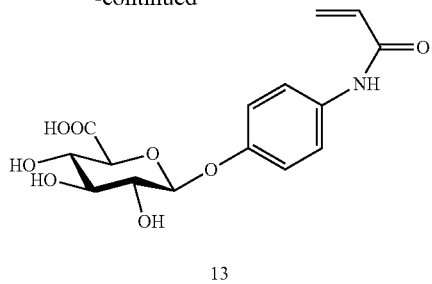

13

<sup>a</sup>Reaction conditions: (a) (i) Pd/C, cHCl, H₂, MeOH:H₂O = 1:1, room temperature, 18 h; (ii) Acryloyl chloride, K₂CO₃, THF:H₂O = 1:2, 0° C. to room temperature, 10 h; (iii) Na form ion exchange resin, H₂O, room temperature, 24 h, 70% (in 3 steps).

p-(N-Acrylamido)phenyl β-D-glucuronic acid (13): 13 was prepared starting from p-nitrophenyl β-D-glucuronide was described previously (Miura, Y. et al., Bulletin of the Chemical Society of Japan (2010) 83:1004-1009).

Preparation of NPs

NPs were synthesized of by free-radical copolymerization of N-isopropylacrylamide (NIPAm) cross-linked with 2 mol % N,N'-methylenebisacrylamide (Bis). N-t-butylacrylamide (TBAm) and 3-sulfo-N-acetylglucosamines (3S), 4-sulfo-N-acetylglucosamines (4S), 6-sulfo-N-acetylglucosamines (6S) or 3,4,6-sulfo-N-acetylglucosamines (3,4,6S) were used as hydrophobic and negatively charged functional monomers. NIPAm (98-(W+X+Y+Z) mol %), NIPAm (W mol %), GlcNAc (X mol %), TBAm (Y mol %), BIS (2 mol %), and SDS (10 mg) were dissolved in water (50 mL) and the resulting solutions were filtered through a no. 2 Whatman filter paper. TBAm (Z mol %) was dissolved in ethanol (1 mL) before addition to the monomer solution, which resulted in a total monomer concentration of 6.5 mm. The resulting solutions were degassed in a sonication bath under vacuum for 10 min and then nitrogen was bubbled through the reaction mixtures for 30 min. Following the addition of ammonium persulfate aqueous solution (30 mg per 500 μL), the polymerization was carried out at 65° C. for 3 h under a nitrogen atmosphere. The polymerized solutions were purified by dialysis against an excess amount of pure water (changed more than twice a day) for >4 days.

Characterization of NPs

The hydrodynamic diameter of NPs was determined in aqueous solution by dynamic light scattering (DLS) (Zeta-sizer Nano ZS). The temperature of the NP samples was controlled via Peltier device at 25±0.1° C. Yield and concentration of NPs was determined by measuring weight of NP after lyophilization.

Quantification of GlcNAc Monomers in NPs by 1H-NMR

In order to determine the ratio of TBAm, NIPAm, and GlcNAc in the polymer, ¹H NMR spectroscopy was utilized using an acquisition time of 30 seconds, respectively. NMR spectra were acquired in CD₃OD and the chemical shifts are reported in ppm on the δ scale reference to residual CD₂HOD (δ 3.31 ppm). The incorporation ratio of GlcNAc and TBAm to NIPAm in the polymer was calculated from the integration of the methyl proton resonances at 1.36 (Tp), 1.16 ppm (Np), 6.99 ppm (Gp) using the equation TBAm:NIPAm:GlcNAc=(Tp/9):(Np/6):(Gp/2).

For all of the samples analyzed, integration of the signals of the methyl proton of the benzene, tert-butyl and isopropyl groups from the NMR spectroscopic data was consistent with the feed ratio. Although no analytical data could be obtained to quantify the incorporation of BIS in the polymer, it was assumed that the feed ratio of the BIS (Bfeed) to other acrylamide monomers prior to polymerization reflected the incorporation ratio of these monomers in the polymer, because incorporation ratio of other amides (GlcNAc, TBAm and NIPAm) were consistent with the feed ratio. This relationship was used to approximate the incorporation of GlcNAc in all of the NPs synthesized in this study (FIG. 1A through FIG. 1D).

Quartz Crystal Microbalance (QCM) Analysis

An Affinix Q⁴ QCM instrument (Initium Co. Ltd., Tokyo, Japan) was used to quantify interactions between the NPs and proteins. At first, gold electrodes were cleaned with piranha solution for 5 min, twice. 3,3'-Dithiodipropionic acid (1 mM, 0.1 mL) was added into the QCM cells and incubated for overnight. Then, the QCM cells were washed with pure water and carboxylic acids on electrodes were activated by loading of 1-ethyl-3-(3-dimethylaminopropyl)-carbodiimide (100 mg/ml) and N-hydroxysuccinimide (100 mg/mL) 1:1 aqueous solution (0.1 mL) to form N-hydroxysuccinimidyl esters. Protein solutions were loaded on the cells to give protein-immobilized cells.

For immobilization of mouse VEGF₁₆₅, the proteins (30 μg/mL) diluted by dH₂O was added onto QCM gold surface (10 μL) and incubated for 3 h at 37° C. Then, the QCM cells were washed with pure water for 2 times, and blocked with 1 mg/mL BSA solution for 1 h. NPs were added into the cells at concentrations of 1.99, 5.9, 13.6, 28.3, 55.2, 100.6, and 168.43 μg/ml. Interactions between NPs and proteins were observed at (37±0.1°) C. in PBS (pH 7.4). The apparent dissociation constant of NPs to protein was calculated under the assumption that all particles have the same affinity to protein.

Cell Culture

Human umbilical vein endothelial cells (HUVECs, Takara Bio Inc., Otsu, Shiga, Japan) were maintained in endothelial growth medium-2 (EGM-2, Cambrex Corporation, Walkersville, Md., USA) at 37° C. under 5% CO₂ in a humidified chamber.

Cell Proliferation and Cytotoxicity Assay

HUVECs were treated with NPs and VEGF₁₆₅ (20 ng/mL) for 48 h. Tetracolor ONE™ (Seikagaku, Tokyo, Japan) was added to each well in accordance with the manufacturer's instructions. The amount of formazan was measured with a Tecan Infinite M200 micro plate reader at a test wavelength of 450 nm and a reference wavelength of 630 nm.

Western Blotting

HUVECs were seeded onto 6 well plates at a density of 2×10⁵ cells/well and incubated overnight. The culture medium was then changed to EBM-2 without growth factors and serum. Twelve hours after the medium change, cells were incubated with EBM-2 containing 20 ng/mL of VEGF₁₆₅ and different concentration of NPs for 2 h at 37° C. For negative control, cells were incubated with only EBM-2 (no VEGF₁₆₅ and NPs). The cells were then washed with PBS and lysed with lysis buffer composed of 10 mM Tris (pH 7.5), 0.1% SDS, 50 μg/mL aprotinin, 200 μM leupeptin, 2 mM PMSF, 100 μM pepstatin A and 1 mM Na₃VO₄. The total protein concentration was measured by using a BCA Protein Assay Reagent Kit (PIERCE Biotechnology, Rockford, Ill.). The cell extracts were subjected to 7.5% SDS-PAGE and transferred electrophoretically to polyvinylidene difluoride (PVDF) membranes (Millipore, Billerica, Mass., USA). After having been blocked for 1 h at room temperature with 5% BSA in Tris-HCl-buffered saline containing 0.1% Tween 20 (TTBS, pH 7.4), the membranes were incubated with a primary antibody (against β-actin, VEGF receptor-2 or pVEGF receptor-2 [Tyr 951]) for 24 h at 4° C. The membranes were then incubated for 1 h at room temperature with HRP-conjugated secondary antibody at a dilution of 1:2000. Each sample was developed by using a chemiluminescent substrate (ECL; GE Healthcare Bioscience), and each protein was detected with the LAS-3000 mini system.

Cell Proliferation and Cytotoxicity Assay

HUVECs were seed on gelatin-coated 96 well plate at $5.0 \times 10^3$ cells/well and incubated overnight. Then, the culture medium was changed to endothelial basal medium-2 (EBM-2, Clonetics) without fetal bovine serum (FBS, Clonetics) and growth factors. Twelve hours after the changing of medium, the cells were treated with NPs and $VEGF_{165}$ (20 ng/mL) for 48 h. For cytotoxicity assay, the cells were treated with only NPs for 48 h. Finally, Tetracolor ONE™ (Seikagaku, Tokyo, Japan) was added to each well in accordance with the manufacturer's instructions. The amount of formazan formed in 3 h was measured with a Tecan Infinite M200 micro plate reader at a test wavelength of 450 nm and a reference wavelength of 630 nm.

Motility and Invasion Assays

HUVECs in serum-free EBM-2 were fluorescently labeled with 3 mM 3'-O-acetyl-2'-7'-bis(carboxyethyl)-4 or 5-carboxyfluorecein, diacetoxymethylester (BCECF-AM, Dojindo Laboratories, Kumamoto, Japan) for 30 min at 37° C. and then washed with PBS. The cells ($5 \times 10^4$ cells in 300 mL of EBM-2) were applied to a FALCON HTS FluoroBlok™ Insert (BD, Franklin, Lakes, N.J., U.S.A.), non-coated for the motility assay or pre-coated with BD Matrigel (125 mg/insert, BD) for the invasion assay. Each culture insert was set into a well containing 700 mL of EBM-2 supplemented with $VEGF_{165}$ (20 ng/mL) with or without NPs (30 µg/mL). The inserts were incubated for 24 h at 37° C. After the incubation, the FluoroBlok membrane was picked up and placed on a glass slide, and the cells that invaded to the lower side of the membrane were observed under a fluorescence microscope (IX71, Olympus, Tokyo, Japan) equipped with a CCD camera (Penguin 600CL, Pixera, Osaka, Japan).

Capillary Tube Formation Assay

Matrigel (BD Biosciences Bedford, Mass.) was diluted to 4 mg/mL with EBM-2 added to 24-well culture plates, and allowed to undergo polymerization. HUVECs were seeded onto Matrigel coated plate at the concentration of $5 \times 10^4$ cells/well. Then, the HUVECs were added $VEGF_{165}$ (20 ng/mL) or/and NPs (30 µg/mL) and were incubated for 12 h at 37° C. Photographs were taken with an Olympus IX71 microscope.

Experimental Animals and In Vivo Matrigel Plug Assay

Five-week-old BALB/c male mice were purchased from Japan SLC Inc. (Shizuoka, Japan). BALB/c-male mice (n=3) were subcutaneously injected with a liquid Matrigel (6 mg/mL) diluted by PBS (700 µL/mouse). The Matrigel contained 20 nM mouse $VEGF_{165}$ and 42 Units of heparin (Ajinomoto Pharmaceuticals Co., Ltd Japan) to stimulate angiogenesis, and NPs at a final concentration of 300 µg/mL. Matrigel and PBS or mouse $VEGF_{165}$ and heparin were injected as negative and positive controls, respectively. After 10 days, Matrigel plugs were removed and photographed. To measure the hemoglobin in the Matrigel, the Matrigel was diluted by PBS and homogenized. The homogenized Matrigel (30 µL) was incubated with 95% glacial acetic acid (120 µL) for 20 min. After the incubation, the sample was centrifuged (5 min, 5000×g) and 30 µL of supernatant was added to 120 µL of 5 mg/mL 3,3',5,5'-tetramethylbenzidine (TMB, Sigma) diluted with 95% glacial acetic acid. Hydrogen peroxide (150 µl of 0.3%, Sigma) was added to each well and the absorbance was measured with a Tecan Infinite M200 micro plate reader at 600 nm.

Statistical Analysis

Differences in a group were evaluated by an analysis of variance (ANOVA) with the Tukey post hoc test.

The results are now described.

Synthesis of Sulfonated and Sulfated Monomers and their Incorporation into Polymer Nanoparticles The strategy employed was to identify several domains of $VEGF_{165}$ and synthesize NPs that incorporate complimentary functional monomers to interact with those domains. Although no structural information of the $VEGF_{165}$-heparin complex is available, Arg 124, 145, 149 and 159 in the $VEGF_{165}$ sequence are known to play a crucial role in heparin binding (Robinson, C. J. et al., J Biol. Chem. (2006) 281:1731-1740). This positive charge-rich domain is spread over 40 nm². To target this domain, a series of polymerizable sulfonated and sulfated monomers were prepared. The monomers include 2-acrylamido-2-methylpropane sulfonic acid (AS), three positional isomers of mono-sulfated N-acetylglucosamines (3 S-GlcNAc, 4S-GlcNAc, 6S-GlcNAc) and a tri-sulfated N-acetylglucosamine (3,4, 6S-GlcNAc). Their structures are shown in FIG. 1B. Solutions of polymer NPs were prepared by a modified precipitation polymerization and purified by extensive dialysis. Each NP contained one of the anionic monomers, in addition to N-isopropylacrylamide (NIPAm), N-tert-butylacrylamide (TBAm, a hydrophobic monomer), and 2% N, N'-methylenebisacrylamide (Bis, a crosslinker) (FIG. 1A). Inclusion of the hydrophobic TBAm monomer was based upon crystallographic studies of the VEGF-VEGFR2 binding surface which has a number of hydrophobic amino acids that play an important role in VEGFR binding (Brozzo, M. S. et al., Blood (2012) 119:1781-1788) and previous studies that established the importance of hydrophobic content of the NP for protein affinity (Hoshino, Y. et al. P Natl Acad Sci USA (2012) 109:33-38; Lee, S. H. et al., J. Am. Chem. Soc. (2012) 134:15765-15772; Yoshimatsu, K. et al., Angew. Chem. Int. Ed. (2012) 51:2405-2408; Hoshino, Y. et al., Small (2009) 5:1562-1568; Hoshino, Y. et al., J. Am. Chem. Soc. (2010) 132:6644-6645). Summaries of NP composition, particle size, -potential, chemical yield and incorporation percentage of the anionic monomers (NMR analysis) are given in FIG. 2A through FIG. 2E and FIG. 3A through FIG. 3D. The monomodal hydrogel particles ranged in size from 30-90 nm. FIG. 1C and FIG. 1D are representative TEM images of the monodisperse synthetic NPs.

Evaluation of NP Affinity to $VEGF_{165}$

Figures 4A, 4B, 4C, 4D:
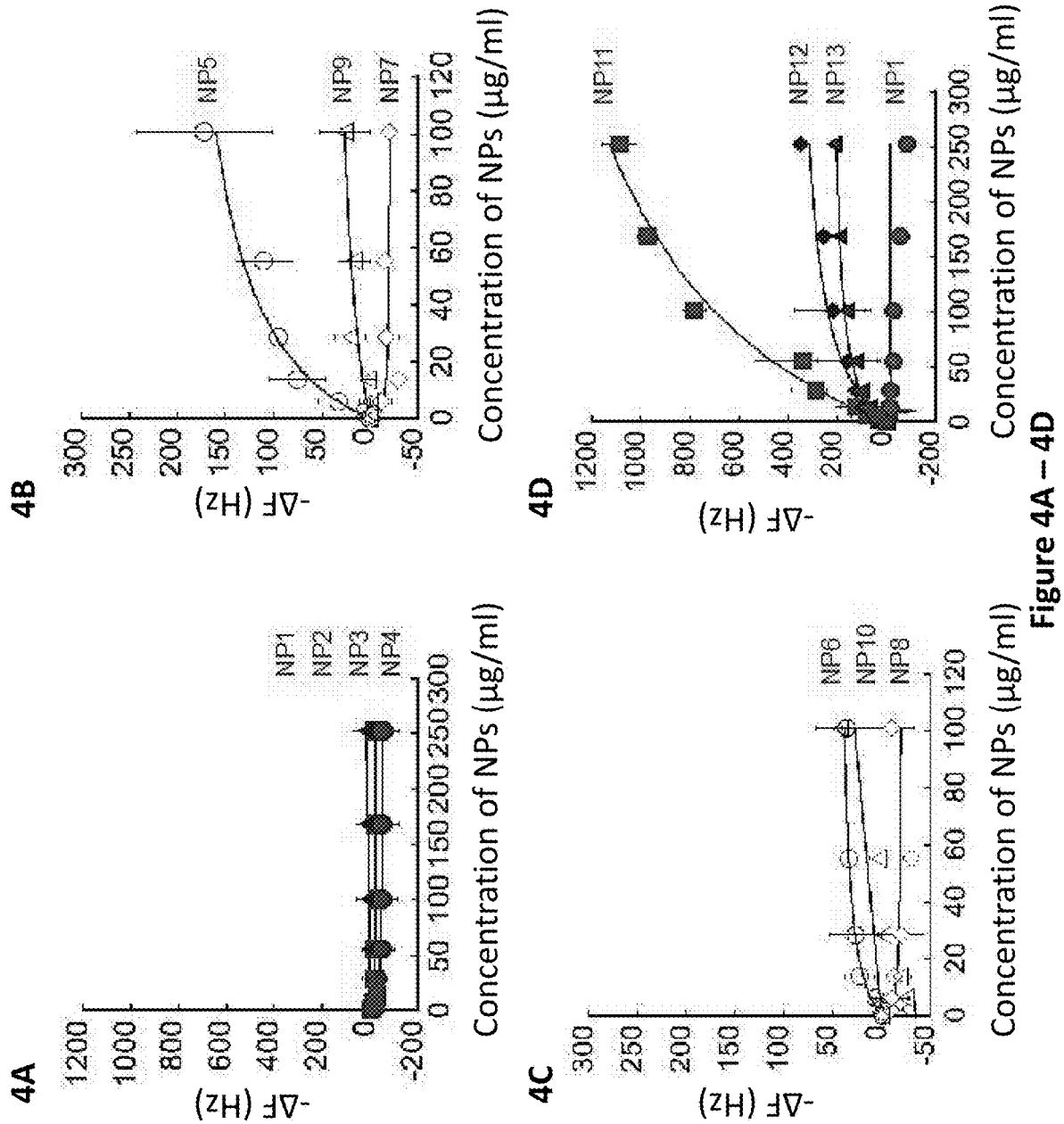
FIG. 4A through FIG. 4D depict the results of screening polymer nanoparticles interacting with $VEGF_{165}$. Quartz crystal microbalance (QCM) was used to analyze $VEGF_{165}$-

A quartz crystal microbalance (QCM) sensor functionalized with $VEGF_{165}$ was used to screen the NP library for protein binding. Interestingly, none of the NPs containing the negatively charged sulfonate group (AS) (NPs 2-4) showed significant binding to $VEGF_{165}$ even when the amount of AS in the NP was increased to 10% (FIG. 4A). Next, NPs containing the 3 S-GlcNAc, 4S-GlcNAc or 6S-GlcNAc (mono-sulfated GlcNAc monomers, NPs 5-10), and the 3,4,6S-GlcNAc (tri-sulfated GlcNAc monomer, NPs 11-13) were screened. These NPs exhibited a wide range of $VEGF_{165}$ interaction. Among NPs 5, 7 and 9 (1.7% of mono-sulfated monomer), only NP5 (1.7% 3S-GlcNAc) exhibited modest $VEGF_{165}$ interaction (FIG. 4B). NPs 6, 8 and 10 (5% of these same mono-sulfated monomers) showed much lower interaction with the protein (FIG. 4C). Collectively, the results establish that NP binding to $VEGF_{165}$ is dependent on the nature of the charged group (sulfate vs sulfonate), the GlcNAc scaffold and the position of sulfation (3' vs 4' or 6'). The sensitivity to the positional isomers on the carbohydrate skeleton may not be surprising as there are a number of studies that report the importance of sulfate position on affinity to target proteins. For example, the 3-O-sulfo group within heparin has been reported to be essential for binding to antithrombin III (Richard, B. et al., J Biol. Chem. (2009) 284:27054-27064), the fibroblast growth factor (FGF)-7 (Ye, S. et al., Biochemistry (2001) 40:14429-14439) and the 6-O-sulfo groups for binding to FGF-1 (Guimond, S. et al., J Biol. Chem. (1993) 268:23906-23914).

Figure 5A:
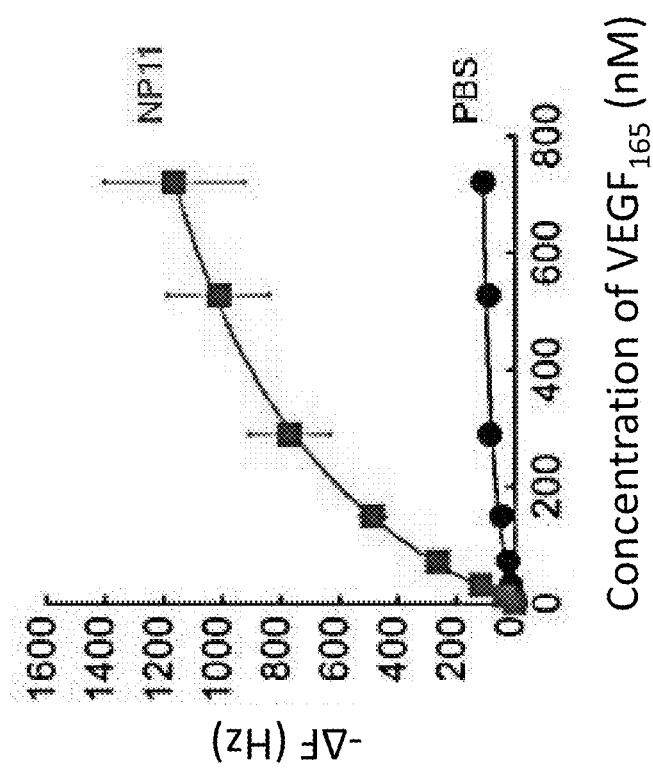
FIG. 5A and FIG. 5B depict the results of QCM analysis of NP-$VEGF_{165}$ interaction.
Figure 5B:
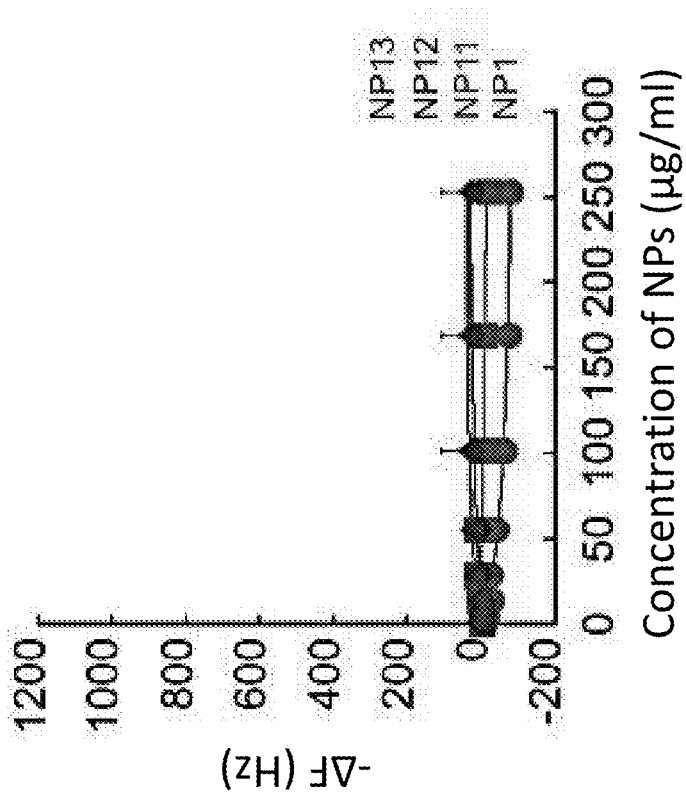
Figures 6A, 6B:
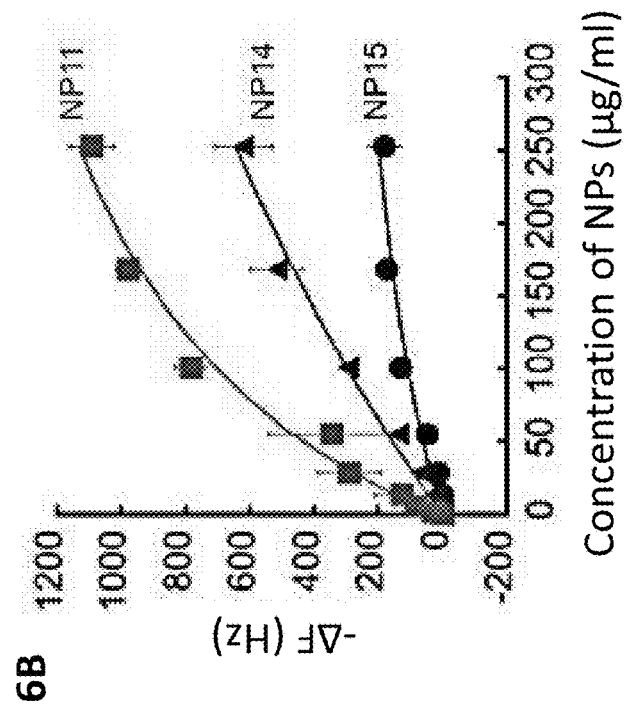
FIG. 6A depicts the monomer composition, size, -potential and yield of the NP11, NP14, and NP15.
FIG. 6B depicts the results of QCM analysis of $VEGF_{165}$-NP interaction. The surface of the QCM was functionalized with $VEGF_{165}$ and solutions of NPs were added to the QCM cells.

The screen of NPs 11-13 incorporating the showed far more dramatic results. Although the particle size and -potential of NPs 11-13 were not significantly different from other NPs tested (FIG. 2A through FIG. 2E), NP11 strongly interacted with $VEGF_{165}$ (FIG. 4D). The observed frequency change (up to 1200 Hz) was 6 times higher than that of NP5. A control study confirmed that the NPs in this study do not interact with the blocking agent (bovine serum albumin, BSA) (FIG. 5A). NP11 affinity is estimated to be ~380 nM (QCM) (FIG. 5B). This result suggests that small local clusters of negative charge from the 3,4,6S-GlcNAc monomer are important for NP binding to $VEGF_{165}$. The significance of hydrophobic groups (TBAm) was established by observing that decreasing the TBAm content of NPs containing 1.7% of the 3,4,6 tri-sulfated GlcNAc monomer from 40% (NP11) to 20% (NP14) to 0% (NP15) significantly reduced and eventually eliminated the interaction with $VEGF_{165}$ (FIG. 6A and FIG. 6B), suggesting that in addition to localized multipoint electrostatic interactions, hydrophobic content is an essential component for the $NP11-VEGF_{165}$ interaction.

Figure 7:
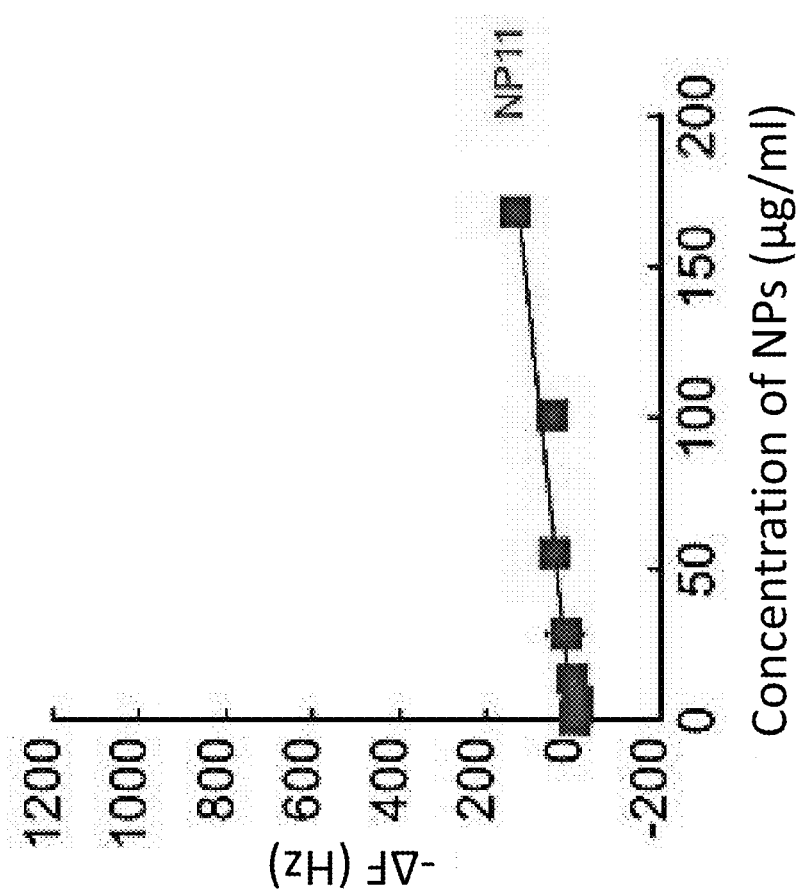
FIG. 7 depicts the results of QCM analysis of VEGF 121-NP interaction. The surface of the QCM was functionalized with VEGF 121 and solutions of NPs were added to the QCM cells.

As stated previously, Arg 124, 145, 149 and 159 in the $VEGF_{165}$ sequence are known to play a crucial role in heparin binding (Robinson, C. J. et al., J Biol. Chem. (2006) 281:1731-1740). It was speculated that NPs incorporating clusters of negative charge, such as the multiple sulfated 3,4,6S GlcNAc group, are effective at binding to this positively charged domain of $VEGF_{165}$. Validation that a significant component of the interaction between $VEGF_{165}$ and NP11 is at the heparin-binding domain comes from QCM studies with $VEGF_{121}$, a truncated growth factor that lacks the heparin-binding domain. NP11 shows little affinity for this protein (FIG. 7). This result coupled with the TBAm results point to the importance of cooperative interactions to realize NP-protein affinity.

That the clustered charge of the tri-anionic monomer may also contribute to the NP-protein affinity comes from comparison with NPs containing an equivalent amount of charged groups using singly charged monomers. These NPs would be less likely to create a "cluster" of negative charge due to electrostatic repulsion of the negative charges in the polymerization step. The constrained triply charged monomer does not suffer from this effect. So, although the net charge of 5% mono-sulfate NPs (NPs 6, 8, 10) and 1.7% 3,4,6S NPs (NP11) is the same, the local presentation of charge in the NP may be significantly different and may be a contributing factor to the difference in affinity. However, these trends are not expected to manifest themselves in zeta potential measurements. A decrease of zeta potential with increase of surface charge density has been observed previously and explained by an ion condensation model. It was predicted theoretically and shown experimentally that for a sufficiently high surface charge density, nearby counter ions can collapse on the particle or polyelectrolyte lowering the effective magnitude of the particle zeta potential (Manning, G. S., Acc. Chem. Res. (1979) 12:443-449; Quesada-Perez, M. et al., J Colloid Interface Sci (2001) 233:280-285; Manning, G. S., Ber Bunsen Phys Chem (1996) 100:909-922; Popov, A. et al., J Polym Sci Pol Phys (2004) 42:3616-3627; Manning, G. S., J Phys Chem B (2007) 111:8554-8559).

Interestingly, both NP12 and NP13 containing a higher percentage of trisulfate monomer 3,4,6S-GlcNAc (5 or 10%) had substantially lower protein interaction compared to NP11. This would appear to be a consequence of the complexity of protein surfaces and the sensitivity to the exact (average) composition of the affinity reagent. In addition to the heparin-binding domain, $VEGF_{165}$ has a number of negatively charged amino acids on its surface. The diminished interaction for $VEGF_{165}$ of NP12 (5%, 3,4,6S-GlcNAc) compared to NP11 (1.7% 3,4,6S-GlcNAc) reflects a needed balance of electrostatic interactions between the protein surface and NP; a higher loading of the tri-anionic 3,4,6S-GlcNAc eventually results in repulsion between the protein and NP. This sensitivity to both charge and hydrophobic contributions calls attention to the uniqueness of each protein (and NP) domain, an attribute that is responsible in part for the selectivity of protein-protein binding in signal transduction and related phenomena.

In Vitro VEGF-Inhibition Experiments and Comparison with Heparin

Figures 8A, 8B, 8C, 8D:
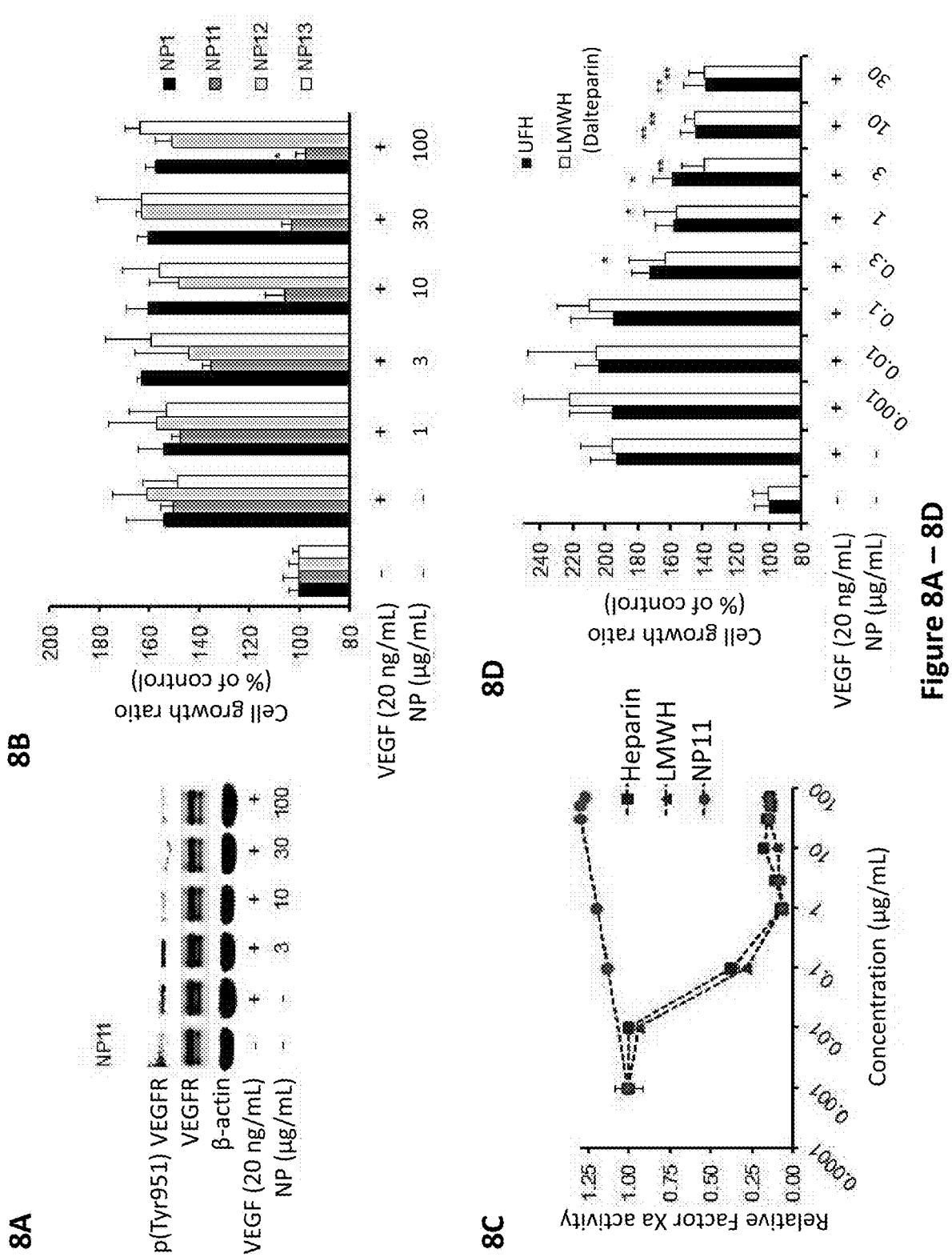
FIG. 8A through FIG. 8D depict the results of in vitro VEGF-inhibition experiments and comparison with heparin.
Figures 9A, 9B, 9C:
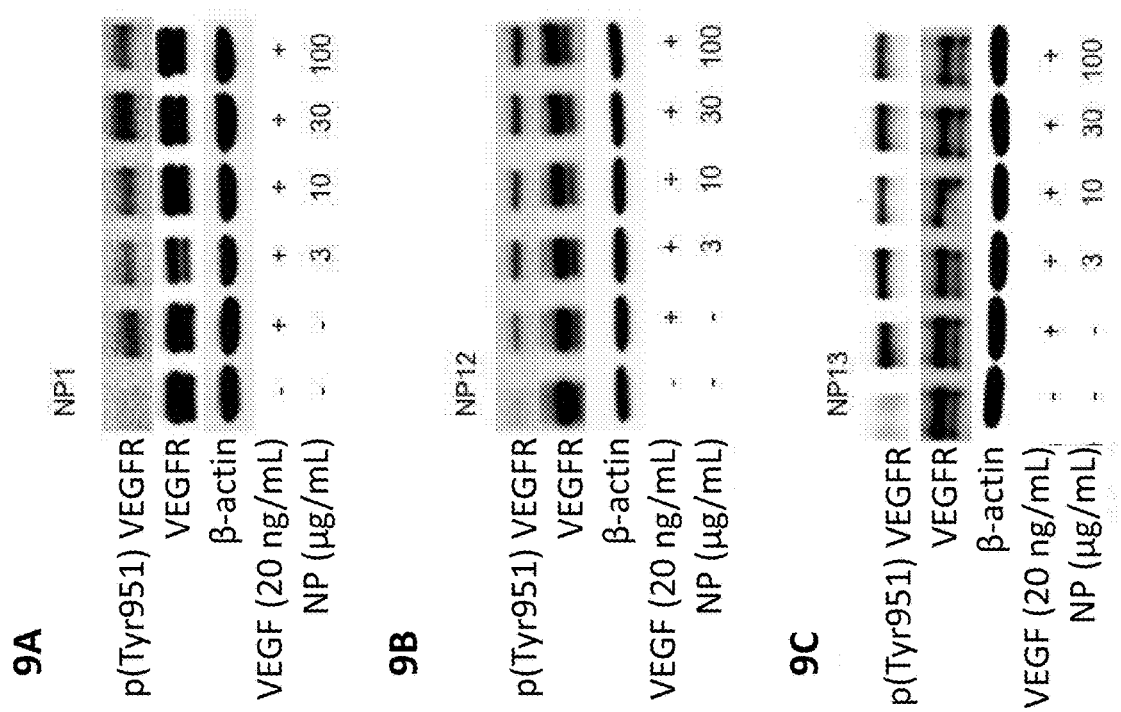
FIG. 9A through FIG. 9C depict the results of experiments demonstrating inhibition of $VEGF_{165}$-dependent VEGFR-2 phosphorylation by NP1, NP12, or NP13. Human umbilical vein endothelial cells (HUVECs) were incubated with EBM-2 containing 20 ng/mL of $VEGF_{165}$ and different concentration of NPs for 2 h at 37° C. The cells were then lysed. The VEGFR and phosphorylated VEGFR (Tyr951) were evaluated by Western blotting.
Figure 10:
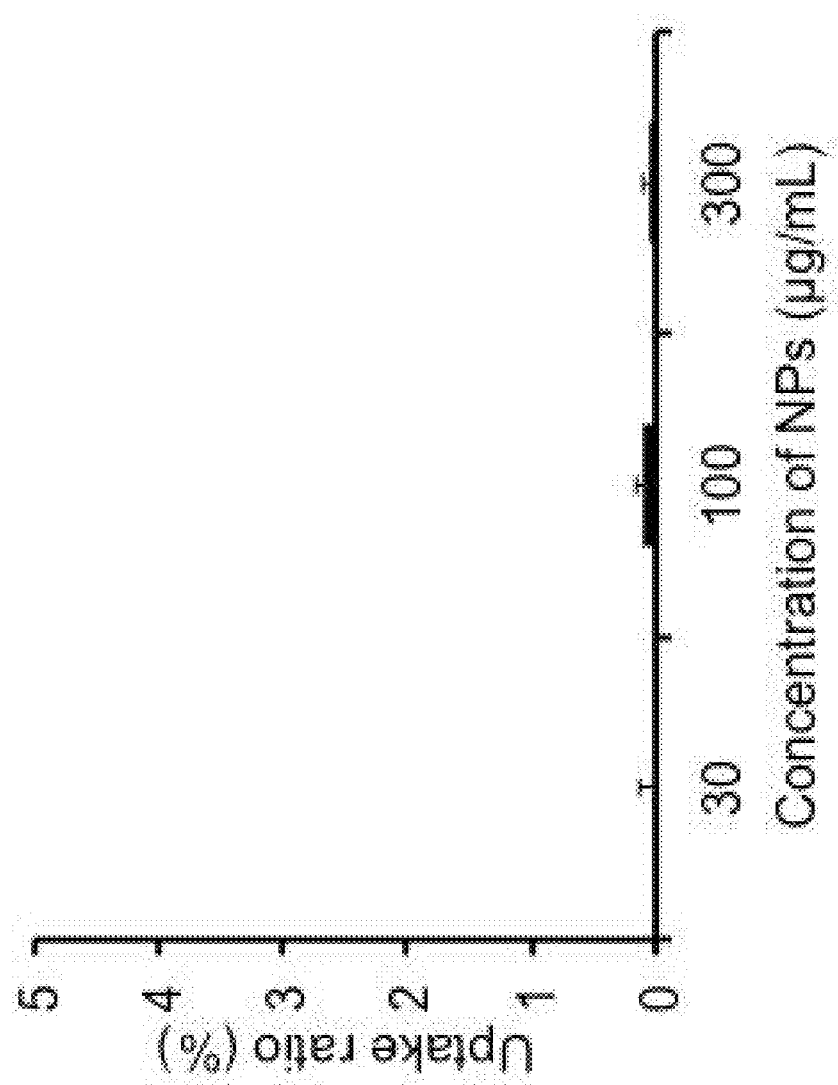
FIG. 10 depicts the results of experiments investigating the uptake of NP11 into HUVEC. HUVECs were incubated with FITC-labeled NP11 for 24 h at 37° C. The cells were then lysed and fluorescence was measured.

Binding of $VEGF_{165}$ to VEGFR-2, its native receptor, is known to induce the phosphorylation of VEGFR-2 and trigger downstream cell signaling events (Graells, J. et al., J Invest Dermatol. (2004) 123:1151-1161). Although there is no direct evidence for the interaction of NP11 with the VEGFR-2 binding domain of $VEGF_{165}$, it was speculated that binding of this relatively large multifunctional NP (~85 nm) with the protein (<10 nm) could antagonize binding to VEGFR-2. An in vitro study was carried out to confirm the inhibitory effect of NP11 on $VEGF_{165}$-induced phosphorylation of VEGFR-2. Human umbilical vein endothelial cells (HUVEC) were incubated with the $VEGF_{165}$ at several concentrations of NPs. NP11 strongly inhibited the phosphorylation ($Tyr_{951}$) at a concentration of 10 µg/mL (FIG. 8A), whereas NP1, NP12 or NP13 did not inhibit the phosphorylation of VEGFR-2 at 100 µg/mL (FIG. 9A through FIG. 9C). It was concluded that NP11 inhibits VEGFR-2 phosphorylation by sequestering $VEGF_{165}$. Phosphorylation of VEGFR-2 is the signaling event for endothelial cell growth. To evaluate the influence of NPs on $VEGF_{165}$-dependent cell growth, $VEGF_{165}$ and NPs were added onto HUVEC. NP11 dose-dependently inhibited $VEGF_{165}$-dependent cell growth, a result that correlates with the phosphorylation inhibition results (FIG. 8B). Indeed, the half maximal inhibitory concentration ($IC_{50}$) of $VEGF_{165}$-dependent HUVEC growth by NP11 was approximately 5 µg/mL. At a concentration of 10 µg/mL, the growth rate was approximately equal to that of control cells without $VEGF_{165}$ (FIG. 8B). These results establish that 10 µg/mL of NP11 effectively inhibits $VEGF_{165}$-dependent phosphorylation and subsequent downstream cell proliferation. Importantly, NP11 was not taken up into the HUVEC even when the NP concentration was increased to 300 µg/ml (FIG. 10).

Figure 11:
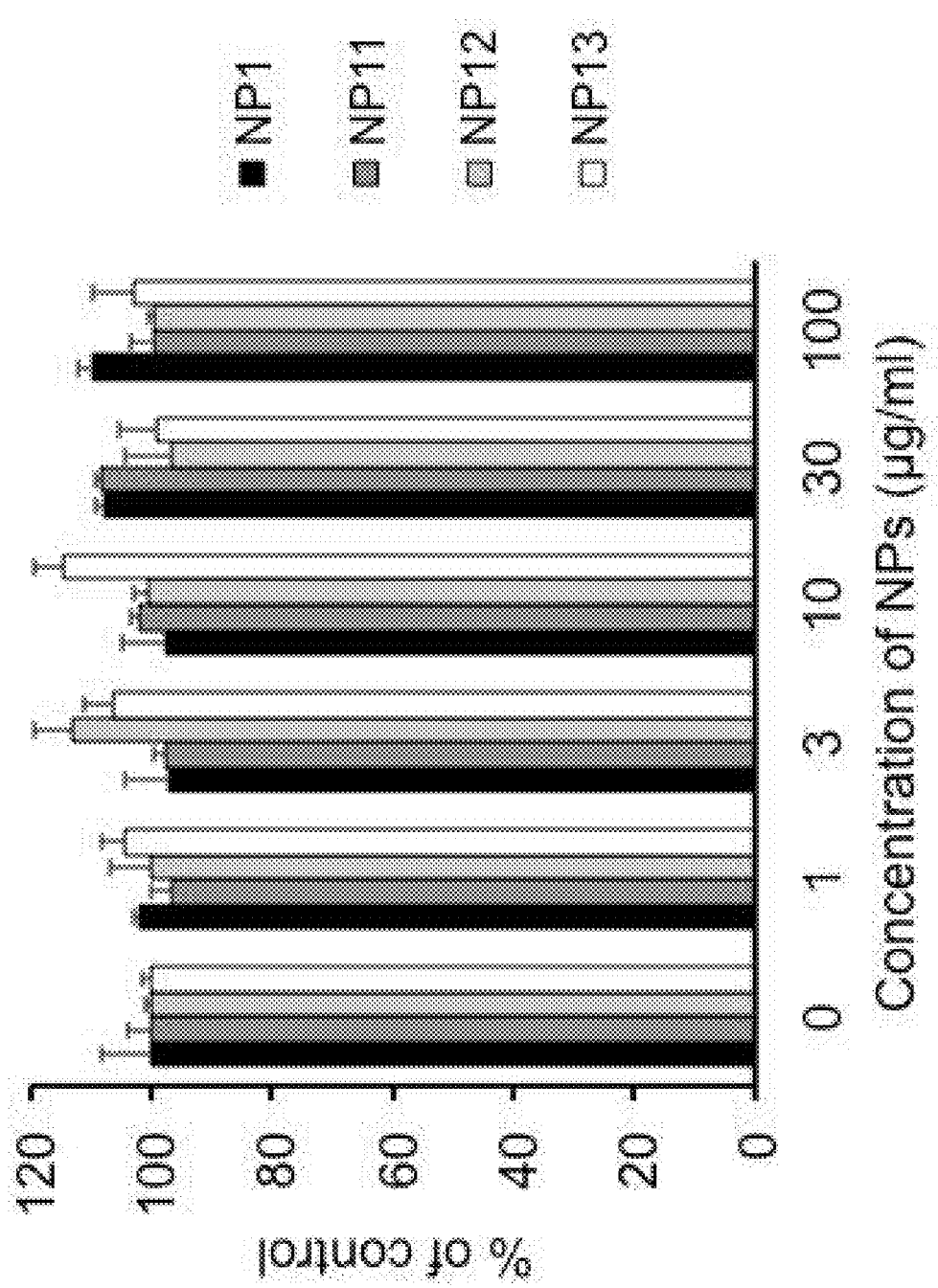
FIG. 11 depicts the results of a cytotoxicity assay of NPs using HUVECs. HUVECs were treated with EGM-2 and various concentrations of NPs. Forty-eight hours after addition, viable cells were determined by MTT assay.

Unfractionated heparin (UFH) or low molecular weight heparin (LMWH, dalteparin) also bind to $VEGF_{165}$. However, these sulfated carbohydrates bind to a number of functional proteins and produce a number of off target outcomes. Perhaps the most important of which is their anti-coagulant activity. For example, following binding of heparin to antithrombin III (AT III), factor Xa (FXa), a key enzyme in the blood coagulation cascade, binds to the complex and induces anti-coagulation. Since NP11 has affinity to the heparin-binding domain of $VEGF_{165}$ it is important to establish if the NP exhibits other heparin-like properties. Significantly, it was found that NP11 does not inhibit the activity of FXa (FIG. 8C). On the other hand, FXa's function was inhibited by heparins. Even at a concentration of 100 µg/mL, NP11 exhibited no inhibition of FXa. The observation demonstrates that although NP11 selectively inhibits $VEGF_{165}$-dependent activity by multiple interactions with both heparin and VEGFR binding domains, it does not interfere with the coagulation cascade. These same studies also established that NP11 did not exhibit cytotoxicity in the range of 0-100 µg/mL (FIG. 11). Since there is little homology in heparin binding domains (Munoz, E. M. et al., Arterioscl Throm Vas (2004) 24:1549-1557), these results demonstrate a potential path to selective abiotic affinity reagents for proteins with heparin binding domains or heparin-mediated processes.

UFH or LMWH also showed a dose-dependent inhibition of $VEGF_{165}$-dependent HUVEC growth (FIG. 8D) with an $IC_{50}$ of 1 µg/mL and 0.3 µg/mL for UFH and LMWH, respectively. However, in contrast to NP11, at those concentrations both UFH and LMWH strongly inhibit FXa, and interfere with the clotting cascade which would result in undesired side effects upon administration (FIG. 8C) (Oh, Y. I. et al., Angew. Chem. Int. Ed. (2013) 52:11796-11799; Warkentin, T. E. et al., N Engl J Med. (1995) 332:1330-1335). These results establish that NP11 is not a heparin mimic and does not exhibit an important heparin function. Its action cannot be replaced by heparin or its derivatives.

Figures 12A, 12B, 12C, 12D:
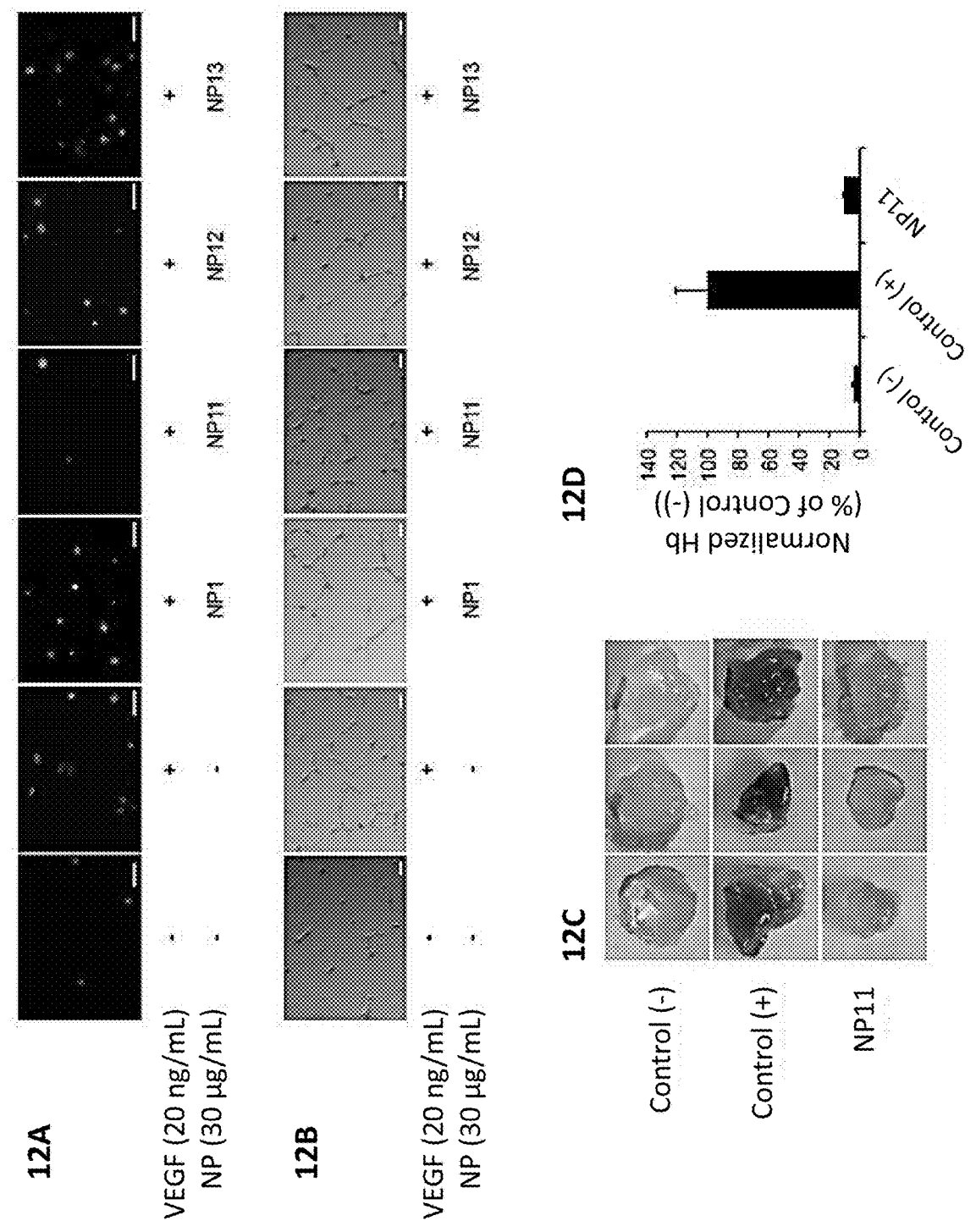
FIG. 12A through FIG. 12D depict the anti-angiogenic effects of NPs.
Figure 13A:
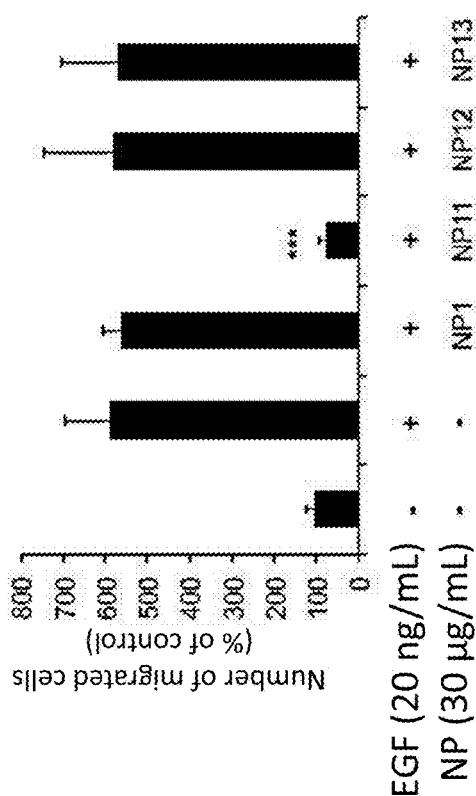
FIG. 13A through FIG. 13C depict the results of experiments demonstrating the inhibition of $VEGF_{165}$-dependent cell motility (FIG. 13A) and invasion (FIG. 13B, FIG. 13C) by NPs. The number of cells that had invaded through the insert was counted under a fluorescence microscope. Significant differences: $***p<0.001$ vs. Control (+) Bar: 30 µm.
Figure 13B:
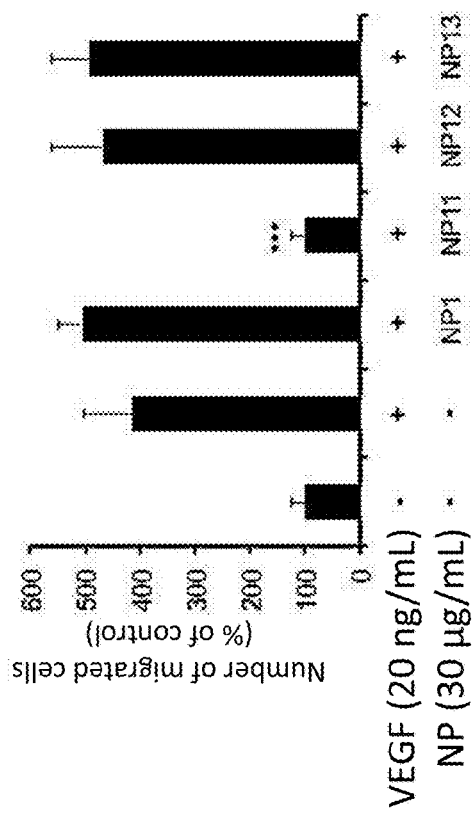
Figure 13C:
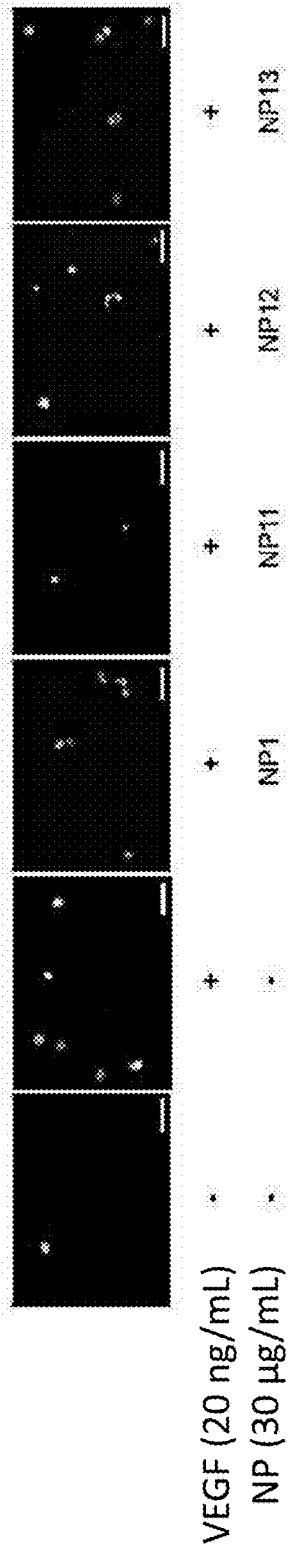
Figure 14:
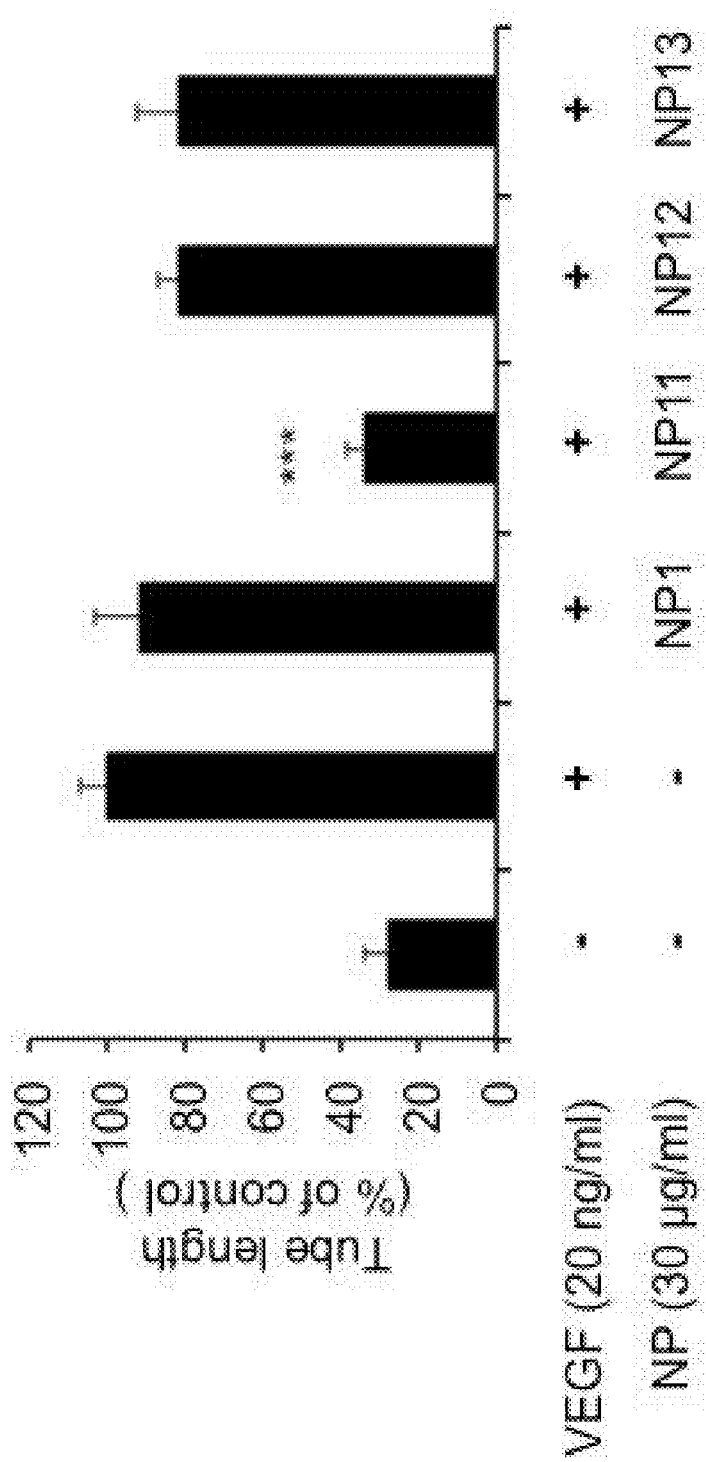
FIG. 14 depicts the results of experiments demonstrating the inhibition of $VEGF_{165}$-dependent capillary tube formation in the presence of NPs. The length of tubes was calculated by using the software Image J. Significant differences: $***p<0.001$ vs. only VEGF.
Figures 15A, 15B, 15C, 15D:
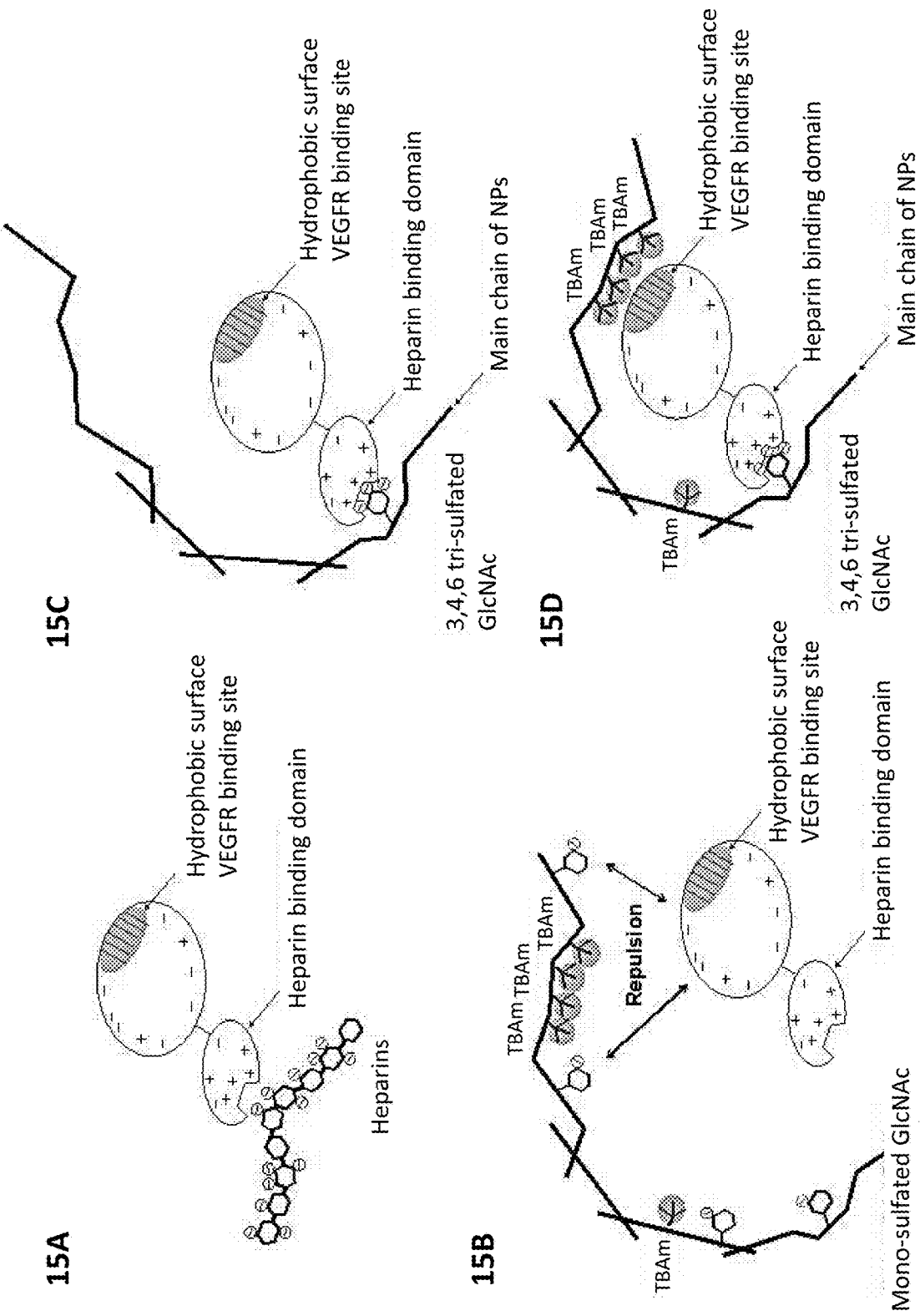
FIG. 15A through FIG. 15D depict schematic images of the interaction of heparins and $VEGF_{165}$ with NPs of various compositions.

Anti-Angiogenic Effect of NPs $VEGF_{165}$ is known to play a major role in angiogenesis and is a critical factor during the early stages of tumor growth (Karamysheva, A. F., Biochemistry (Mosc) (2008), 73:751-762; Carmeliet, P. et al., Nature (2000) 407:249-257; Brekken, R. A. et al., Cancer Res (2000) 60:5117-5124). In angiogenesis, endothelial cell migration and invasion into the extracellular matrix are important steps in the production of angiogenic blood vessels. The effect of NP11 on downstream angiogenic activity was evaluated by experiments that revealed only NP11 (30 µg/mL) significantly inhibits $VEGF_{165}$-induced HUVECs migration and invasion (FIG. 12A, FIG. 13A through FIG. 13C). In addition, tube formation by endothelial cells is the first step in formation of angiogenic blood vessels. HUVECs were seeded onto a Matrigel coated plate and then $VEGF_{165}$ (20 ng/mL) and NPs (30 µg/mL) were added to the medium. HUVECs formed capillary-like structures only upon addition of $VEGF_{165}$. However, the addition of NP11 effectively inhibits the $VEGF_{165}$-induced capillary tube formation (FIG. 12B, FIG. 14). On the other hand, capillary tube formation was not inhibited by NPs with less pronounced $VEGF_{165}$ affinity such as NP1, NP12 or NP13. The inhibition of downstream anti-angiogenic function is a consequence of the sequestration of $VEGF_{165}$ by NP11.

To evaluate the efficacy of NP11 to block new blood vessel formation under more challenging conditions, a Matrigel plug assay was performed. Mice were subcutaneously injected with Matrigel alone, a $VEGF_{165}$/heparin (positive control), or $VEGF_{165}$/heparin and NP11. Ten days after the implantation, Matrigel plugs were removed and the hemoglobin content was measured. As shown in FIG. 12C, incorporation of NP11 into the Matrigel plug effectively inhibited blood vessel formation. Indeed, the hemoglobin content in the Matrigel plug was very close to that of the negative control (absence of $VEGF_{165}$, FIG. 12D). Collectively, these results establish the ability of NP11 to inhibit recruitment of endothelial cells and prevent new blood vessel formation by sequestrating $VEGF_{165}$.

The present study describes a process for synthesizing an abiotic protein affinity reagent. Polymer NPs with affinity for $VEGF_{165}$, a key vascular endothelial growth factor, were identified from a screen of a small library of NPs prepared by copolymerizing monomers with functionality complementary to the heparin and VEGFR-2 binding domains of the protein. Polymer NPs with nanomolar affinity to $VEGF_{165}$ were realized by incorporating 1.7% of a trisulfated N-acetylglucosamine (3,4,6S-GlcNAc) monomer, a hydrophobic group, N-tert-butylacrylamide (TBAm), in a 2% crosslinked NIPAm copolymer. NP affinity was "tuned" by varying the amount of both 3,4,6S-GlcNAc and TBAm monomer incorporation since increasing the 3,4,6S-GlcNAc monomer and/or decreasing the hydrophobic monomer (TBAm) content decreased affinity to the protein. The NP-protein interaction was designed to take place over multiple protein domains (FIG. 15A through FIG. 15D), a factor that was validated by compositional variation of the NP and by screening NP affinity against truncated proteins. The optimized NP (NP11) was shown to inhibit $VEGF_{165}$-dependent growth, tube formation, migration and invasion of HUVECs in vitro through suppression of VEGFR-2 phosphorylation. Importantly, at concentrations needed to inhibit VEGFR-2 phosphorylation, the optimized NP (NP11) did not inhibit the activity of FXa. This result distinguishes the NP from heparin and its derivatives both of which inhibit VEGF-dependent HUVEC growth in addition to enzymes involved in the blood coagulation cascade. NP11 was also shown to inhibit $VEGF_{165}$-dependent angiogenesis in a Matrigel plug in the body of living mice. These results establish that NPs can be engineered to bind to and interfere with a signaling protein ($VEGF_{165}$), by targeting specific domains of the protein by inclusion of both hydrophobic and a novel trisulfated carbohydrate functional group into a 2% cross-linked NIPAm synthetic polymer. The carbohydrate platform permits the stereocontrolled incorporation of clusters of functional groups, a feature not available to amino acid side chains. These results establish the potential for realizing abiotic protein affinity reagents with many of the functions of more traditional protein affinity reagents.

Example 2: An Abiotic Anti-VEGF Nanoparticle for Anti-Angiogenic Cancer Therapy

Tumors require the induction and maintenance of a dedicated blood supply for their growth. Cancer cells secrete a number of growth factors including vascular endothelial growth factor (VEGF) to create new blood vessels in a process known as angiogenesis (Folkman, J., N Engl J Med (1971) 285(21):1182-1186; Folkman, J. et al., J Biol Chem (1992) 267(16):10931-10934). Blocking the VEGF-receptor interaction and inhibiting angiogenesis is a proven therapeutic target for cancer treatment (Ferrara, N. et al., Nature (2005) 438(7070):967-974; Tugues, S. et al., Mol Aspects Med (2011) 32(2):88-111). The following study demonstrates that an abiotic synthetic polymer nanoparticle (NP) with engineered multi point affinity for $VEGF_{165}$, inhibits the VEGF-VEGFR interaction and downstream VEGF-dependent function in vitro. In vivo administration of anti-VEGF NPs suppressed tumor growth and normalized tumor vasculature. Combination therapy with doxorubicin was found to result in increased doxorubicin concentration in the tumor and dramatic inhibition of tumor growth. This biologically inspired nanoparticle establishes a new paradigm for inhibiting protein-protein interactions using synthetic polymer nanoparticles and points the way to alternative, inexpensive, abiotic angiogenesis inhibitors.

Just as medicinal chemists routinely design and synthesize small drug molecules that bind to the active site of a target protein, advances in polymer synthesis, structural biology and nanotechnology have progressed to the point where synthetic polymer nanoparticles (NPs) can be designed with high affinity and selectivity for a targeted protein. The present study describes an abiotic synthetic polymer nanoparticle that functions as a protein capture agent, a "plastic antibody", and its therapeutic application in vivo. These results establish the potential for inexpensive synthetic polymer nanoparticles as inhibitors of protein-protein interactions that are involved in signal transduction and may point the way to abiotic, cost effective anti-angiogenic agents for treatment of certain cancers.

The emergence of protein therapeutics marks an important advance in modern medicine. Many protein therapeutic agents exploit the selectivity and affinity of antibodies to modulate or inhibit protein function. The number of FDA approved protein drugs and those at various stages of clinical trials attest to the vitality of the field and is a measure the efficacy of this strategy (Mullard, A., Nat Rev Drug Discov (2013) 12(5):329-332). Despite their significant role in contemporary medicine, the costs of discovery and production of humanized antibodies can place a burden on the health care system. It is anticipated that the costs of these proteins will be reduced in time making them more widely available. Nevertheless new strategies, particularly those that could rapidly produce efficacious candidates without the use of living organisms and at lower cost, warrant consideration as potential alternatives. Previous studies have demonstrated that a synthetic polymer hydrogel nanoparticle (NP), made by copolymerization of monomers containing functional groups complimentary to those of a target peptide toxin melittin, bind the toxin with low nanomolar affinity (Hoshino, Y. et al., J Am Chem Soc (2008) 130(46):15242-15243; Hoshino, Y. et al., Small (2009) 5(13):1562-1568). In vitro and in vivo studies of the anti-toxin NPs, established a dose dependent inhibition of cytotoxicity providing the potential for an abiotic treatment of injuries and diseases caused by peptide toxins (Hoshino, Y. et al., J Am Chem Soc (2010) 132(19):6644-6645; Hoshino, Y. et al., Proc Natl Acad Sci USA (2012) 109(1):33-38). Subsequent studies revealed the NPs sequester and clear the toxin neutralizing its activity (Hoshino, Y. et al., Proc Natl Acad Sci USA (2012) 109(1):33-38; Hu, C. M. et al., Nat Nanotechnol (2013) 8(5):336-340; Smith, M. H. et al., Macromolecules (2011) 44(20):8154-8160). It has also been established that NPs can be formulated to recognize and bind to a specific domain of large proteins (IgG, lysozyme) (Lee, S. H. et al., J Am Chem Soc. (2012) 134(38):15765-15772; Yoshimatsu, K. et al., Angew Chem Int Ed Engl (2012) 51(10):2405-2408). These results establish the efficacy of synthetic polymer NPs both in vitro and in vivo settings and call attention to the potential for their use as alternative, stable protein affinity ligands for diagnostics, research tools in molecular biology, drug delivery, disease therapy, and as antidotes for toxins and viruses (Hoshino, Y. et al., Proc Natl Acad Sci USA (2012) 109(1):33-38; Hu, C. M. et al., Nat Nanotechnol (2013) 8(5):336-340).

The following study describes a synthetic polymer hydrogel nanoparticle engineered to bind to a vascular endothelial growth factor (VEGF) and its potential for anti-angiogenic therapy. Angiogenesis is induced by several growth factors, most importantly $VEGF_{165}$, a 165 amino acid protein (39.2 kDa, pI=7.6). Inhibition of the function of $VEGF_{165}$ is an attractive strategy for anti-cancer therapy because tumors can be induced to apoptosis by reducing or shutting down the blood supply of nutrients and oxygen (Cao, Y., Semin Cancer Biol (2004) 14(2):139-145). An important example is Avastin® (bevacizumab), an anti-VEGF monoclonal antibody approved by the FDA in 2004.

Avastin® targets the VEGF receptor-binding domain and is proposed to competitively inhibit the binding of VEGF to its receptors (VEGFR-1 and 2). $VEGF_{165}$ and VEGFR-2 binding is attributed in part to hydrophobic interactions including Phe17, Ile43, Ile46, Ile83 and Pro85 of VEGF-A15. It is also known that $VEGF_{165}$ has a heparin-binding domain. Heparin, a highly sulfated carbohydrate comprised of N-acetylglucosamine units, binds to $VEGF_{165}$ through Arg 124, 145, 149 and 159 in the $VEGF_{165}$ sequence 16. It has been proposed that the heparin-binding domain assists the binding of $VEGF_{165}$ to VEGFR-217. Here, synthetic polymer NPs containing both hydrophobic and negatively charged groups are optimized for affinity to $VEGF_{165}$. As with related antibody strategies, NP binding to $VEGF_{165}$ could inhibit its function.

The materials and methods used in these experiments are now described.

Preparation of NPs

NPs were synthesized of by free-radical copolymerization of N-isopropylacrylamide (NIPAm) cross-linked with 2 mol % N,N'-methylenebisacrylamide (Bis). N-tert-butylacrylamide (TBAm) and 3-sulfo-N-acetylglucosamines (3S), 4-sulfo-N-acetylglucosamines (4S), 6-sulfo-N-acetylglucosamines (6S) or 3,4,6-sulfo-N-acetylglucosamines (3,4, 6S) were used as hydrophobic and negatively charged functional monomers. The polymerization was carried out at 65° C. for 3 h under a nitrogen atmosphere. The polymerized solutions were purified by dialysis.

Characterization of NPs

The hydrodynamic diameter of NPs was determined in aqueous solution by dynamic light scattering (DLS) (Zetasizer Nano ZS).

Quantification of GlcNAc monomers in Nps by $^1$H-NMR

In order to determine the ratio of TBAm, NIPAm, and GlcNAc in the polymer, $^1$H NMR spectroscopy was utilized using an acquisition time of 30 seconds, respectively.

Quartz Crystal Microbalance (QCM) Analysis

An Affinix $Q^4$ QCM instrument (Initium Co. Ltd., Tokyo, Japan) was used to quantify interactions between the NPs and proteins.

Experimental Animals

Five-week-old BALB/c male mice were purchased from Japan SLC Inc. (Shizuoka, Japan). The animals were cared for according to the Animal Facility Guidelines of the University of Shizuoka. All animal experiments were approved by the Animal and Ethics Review Committee of the University of Shizuoka.

Histological Assessment of Liver

Five-week-old BALB/c-male mice (n=3) were intravenously injected with NP11 (40 mg/kg). Two weeks after the injection, the liver sections were stained with hematoxylin and eosin. Photographs were taken with an Olympus IX71 microscope.

Measurement of TNF-α and IL-12

Five-week-old BALB/c-male mice (n=4) were intravenously injected with PBS (for negative control), NP11 (40 mg/kg) or lipopolysaccharide (LPS). The serum was collected at 1, 6 and 12 h after the injection. TNF-α and IL-12 levels in the serum were determined using a specific ELISA kit (Mouse TNF-α ELISA kit, R&D systems, MN, U.S.A. and Mouse IL-12 ELISA Kit, BD Biosciences, CA, U.S.A.).

Therapeutic Experiment

Colon26 NL-17 cells (1.0×106 cells/mouse) were subcutaneously inoculated into the posterior flank of 5-week-old BALB/c male mice. Five days after the tumor implantation, these mice were injected with PBS or NPs (5, 10, 20 or 40 mg/kg, 200 µL/mouse) at day 5, 7, 9 and 11 after the tumor inoculation. For combination therapy, the mice were injected with NPs (20 or 40 mg/kg, 200 µL/mouse) at day 5, 7, 9 and 11, and doxorubicin (2.5 or 5 mg/kg, 200 µL/mouse) at day 6, 8, 10 and 12 after the tumor inoculation. The size of the tumors and the body weight of each mouse were monitored. Calculation of the tumor volume was performed using the formula 0.4×(a×b2).

Tumor Perfusion Analysis

To analyze the perfusion efficiency, the mice were intravenously injected with 100 µl of 1 mg/ml biotinylated *Lycopersicon esculentum* (tomato) lectin (Vector laboratories) 24 h after the final NP11 injection. The lectin was circulated for 10 min and mice were perfused with 1% paraformaldehyde in PBS before tumors were collected. Tumor sections were stained with Alexa594-conjugated streptavidin and FITC-conjugated anti-$CD_{31}$ antibody to identify perfused and total vessels, respectively.

Measurement of Dox in Tumor

Tumor-implanted mice were injected with NPs (40 mg/kg, 200 µL/mouse) at day 5, 7, 9 and 11, and doxorubicin (5 mg/kg, 200 µL/mouse) at day 6, 8, 10 and 12 after the tumor inoculation. Four hours after the final Dox injection, the tumors were homogenized in 10 volumes (w/v) of 10 mM phosphate buffer (pH 7.8). Then, the Dox in the tumor was extracted by chloroform:methanol (4:1, v/v). The organic layer was completely dry and re-suspended with 1% formic acid containing $H_2O$:MeOH (1:1, v/v).

Measurement of Dox

The UPLC-ESI-TOF-MS system consisted of an ACQUITY™ ultra-performance lipid chromatography and a Micromass LCT Premier™ XE mass spectrometer (high-sensitivity orthogonal time-of-flight instrument; Waters, Milford, Mass., USA).

Statistical Analysis

Differences in a group were evaluated by an analysis of variance (ANOVA) with the Tukey post hoc test.

The results are now described.

Tumor Growth Inhibition by Combination Therapy of NPs and Dox

Figures 16A, 16B, 16C:
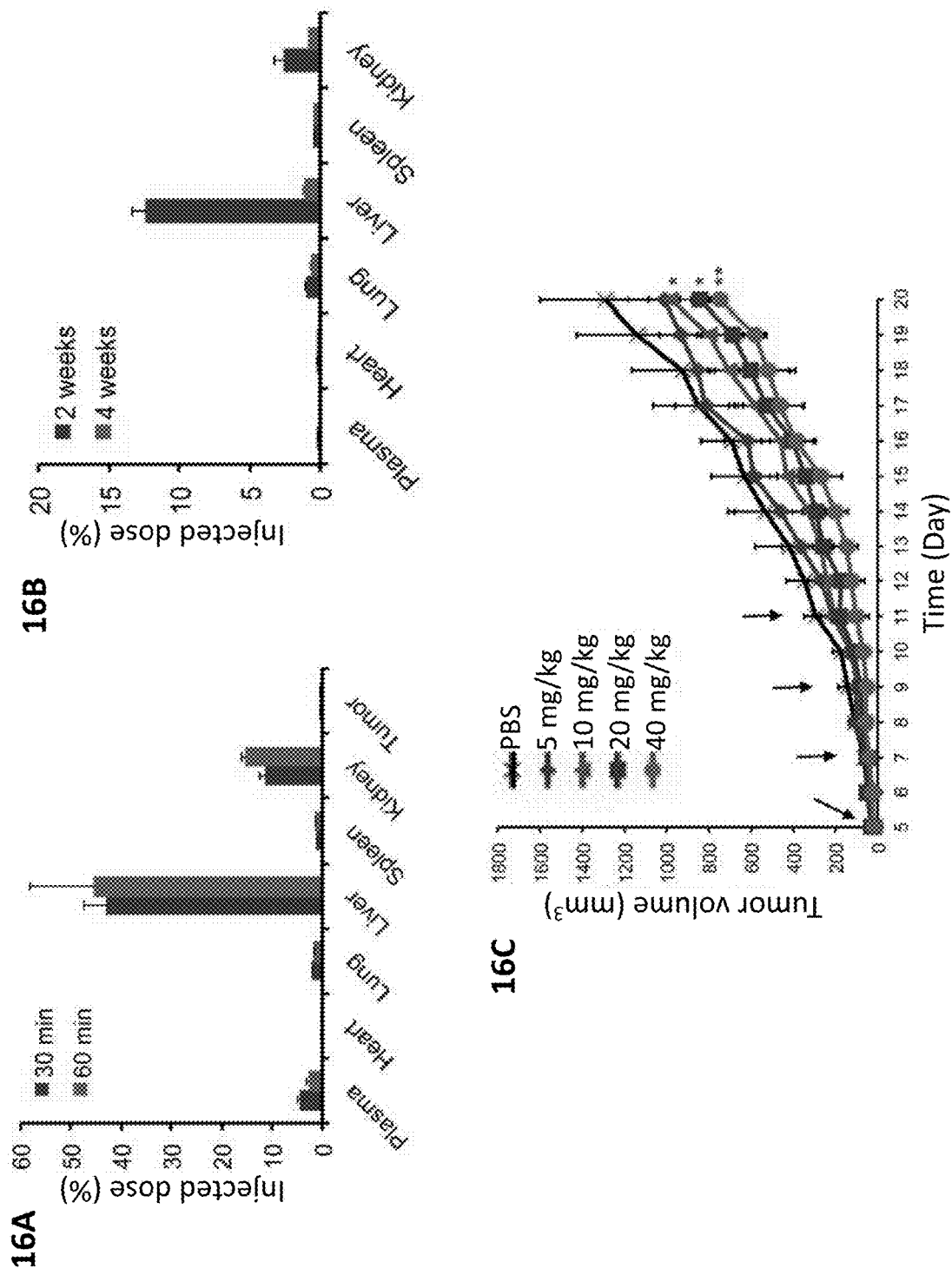
FIG. 16A through 16G depict the results of experiments demonstrating tumor growth inhibition by combination therapy of NPs and Dox.

In vivo anti-angiogenic activity was examined using nanoparticle NP11, which incorporates 1.7% of the 3,4,6S-GlcNAc monomer. In preliminary studies subcutaneously tumor-implanted mice were used to measure the biodistribution of $^{14}$C-labeled NP11 at 30 min or 1 h (FIG. 16A). NP11 accumulated mainly in the liver, and did not accumulate significantly in other organs and in the bloodstream. Histological assessment of the liver indicates that there is no significant difference between PBS and NP11 injection. Furthermore, acute inflammatory cytokines, TNF-α and IL-12, were not significantly upregulated in the plasma by the presence of NP11. Approximately 15% of the injected NP11 remained in the liver and 5% in the kidney 2 weeks after the injection. However, more than 97% of NPs were eliminated from the body at 4 weeks (FIG. 16B). These results indicate that within the therapeutic window of the in vivo experiments, complications arising from immunogenicity and toxicity of NP11 should not be problematic.

To evaluate whether NP11 inhibits tumor growth in vivo by inhibition of angiogenesis, tumor implanted mice were injected with NP11 (5, 10, 20, 40 mg/kg). NP11 significantly inhibited tumor growth without significant body weight changes compared to PBS treatment (FIG. 16C). Only a few % of NP11 exists in the tumor 1 h after intravenous injection. A possible explanation is that NP11 interacts with $VEGF_{165}$ in the vicinity of the tumor where it is sequestered and removed. In addition, the small amount of NP11 that remains in the vicinity of the tumor may continue to clear $VEGF_{165}$ secreted from the tumor.

Figure 16D:
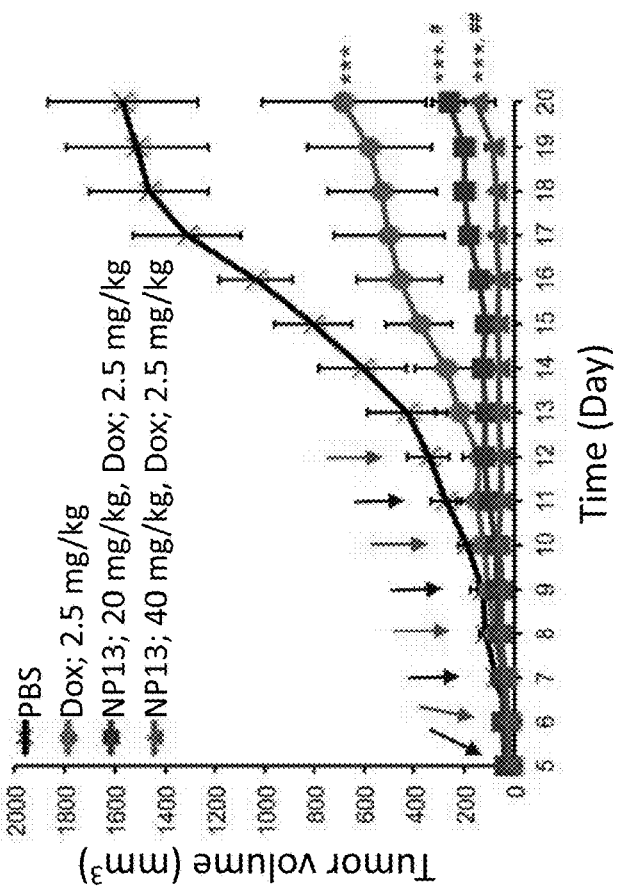
Figure 16E:
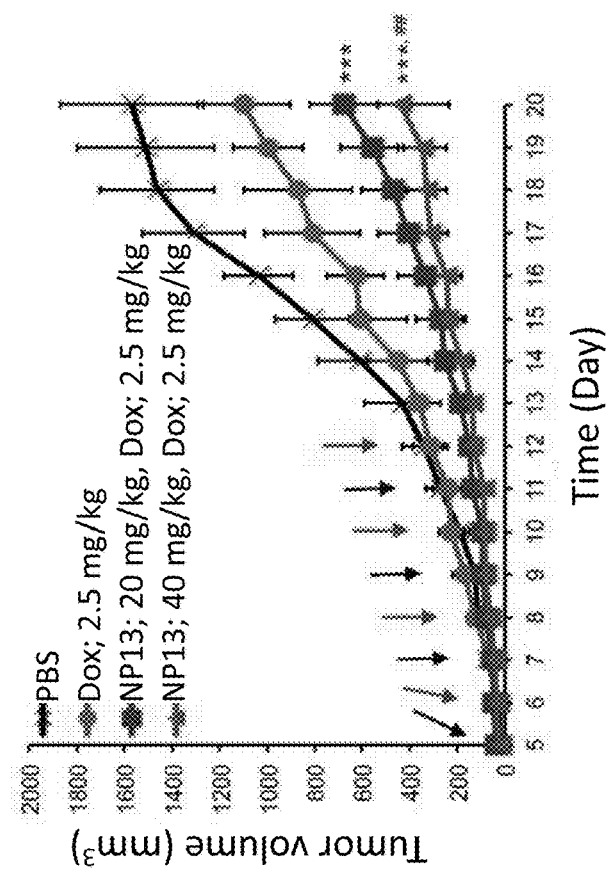

An interesting new concept has emerged suggesting that apart from inhibiting new vessel formation, anti-angiogenic therapy may normalize the established tumor vasculature and increase anticancer drug concentration in the tumor (Park, J. E. et al., Mol Biol Cell (1993) 4(12):1317-1326; Jain, R. K., Science (2005) 307(5706):58-62; Greenberg, J. I. et al., Nature (2008) 456(7223):809-813; Wildiers, H. et al. Br J Cancer (2003) 88(12):1979-1986; Jain, R. K., Nat Rev Cancer (2008) 8(4):309-316). Consistent with this concept, anti-VEGF medicines are frequently used in combination with anti-cancer drugs. This combination therapy often induces a synergistic effect (Singleton, P. A. et al., Mol Cancer Ther (2008) 7(6):1669-1679). To establish if the NPs also induce a synergistic effect, NP11 (20 or 40 mg/kg) and doxorubicin (Dox, 2.5 or 5 mg/kg), an anti-cancer drug, were administered into tumor-implanted mice. Tumor growth was significantly inhibited at Dox concentration levels of 2.5 or 5 mg/kg in combination therapy compared with NP11 or Dox injection alone (FIG. 16D, FIG. 16E). In addition, when therapy was initiated with mice using NP11 (40 mg/kg) and Dox (5 mg/kg), the implanted tumor size did not increase in size until 6 days after the final injection. Some reduction in body weight was noted by combination therapy, which could be due to side effects triggered from the Dox injection.

Figures 16F, 16G:
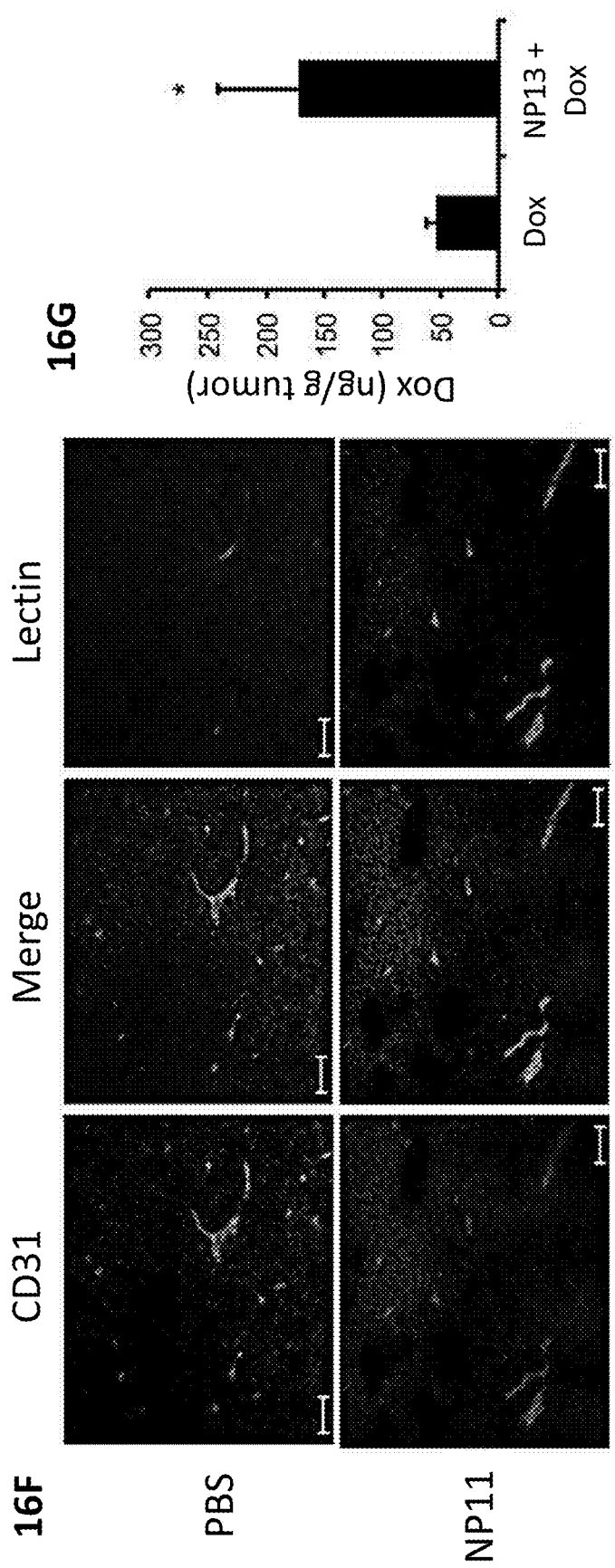

Blood perfusion efficiency was determined following NP11 treatment by intravenous injection of biotin-labeled lectin (before preparation of tumor section) and CD31 (after preparation of tumor section) staining. CD31 staining reveals all blood vessels while biotin-labeled lectin binds to only perfused endothelial cells (FIG. 16F). Tumors treated with PBS show significant numbers of endothelial cells that were not merged with biotin-labeled lectin (CD31 positive and lectin negative). In contrast, NP11 treated tumors show that every endothelial cell was merged with biotin-labeled lectin (CD31 and lectin positive). The tumor vessel perfusion and microvessel density after the NP11 treatment were significantly reduced compared with non-treated tumor. In addition, the concentration of Dox in the tumor was significantly increased by the NP11 injection (FIG. 16G). These results indicate that NP11 disrupted non-effective blood vessel formation and normalized tumor vasculature, and increased Dox accumulation in the tumor.

In summary, a novel abiotic synthetic polymer NP was developed with affinity for $VEGF_{165}$. The NP targeted the heparin-binding domain thru the 3,4,6 trisulfate N-acetylglucosamine. Hydrophobic groups on the NP were also important for its interaction with hydrophobic domains on the surface of VEGF. Optimized non-toxic NPs efficiently inhibited VEGF-VEGFR interactions in vitro and in vivo resulting in suppression of tumor growth. The concept of a synthetic polymer NP interacting with a large area of target protein thru complementary interactions and inhibiting its function should provide strong impetus for efforts to engineer novel bioactive agents for biomedical applications. These abiotic materials have the potential to be used as inexpensive and stable functional materials for applications that include diagnostics, research tools in molecular biology, or for disease therapy and may very well point the way to a novel, abiotic, cost effective anti-angiogenic agent for treatment of certain cancers.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a pharmaceutically acceptable carrier and an abiotic, synthetic cross-linked polymer having affinity to vascular endothelial growth factor (VEGF), comprising:
   N-isopropylacrylamide (NIPAm);
   N-tert-butylacrylamide (TBAm);
   N,N'-methylenebisacrylamide (Bis); and
   a sulfated N-acetylglucosamine (GlcNAc), wherein the polymer comprises between 1% and 3% sulfated GlcNAc.

2. The composition of claim 1, wherein the sulfated N-acetylglucosamine (GlcNAc) is selected from the group consisting of mono-sulfated positional isomer 3S-GlcNAc, mono-sulfated positional isomer 4S-GlcNAc, mono-sulfated positional isomer 6S-GlcNAc, and tri-sulfated 3,4,6S-GlcNAc.

3. The composition of claim 1, wherein the polymer comprises between 30% and 70% NIPAm.

4. The composition of claim 1, wherein the polymer comprises between 30% and 50% TBAm.

5. The composition of claim 1, wherein the polymer comprises between 0% and 10% Bis.

6. The composition of claim 1, wherein the polymer comprises 56.3% NIPAm, 40% TBAm, 2% Bis, and 1.7% tri-sulfated 3,4,6S-GlcNAc.

7. The composition of claim 1, wherein the composition is a nanoparticle.

8. The composition of claim 1, wherein the composition further comprises at least one therapeutic agent.

* * * * *